United States Patent
Muller et al.

(10) Patent No.: US 12,366,543 B2
(45) Date of Patent: Jul. 22, 2025

(54) DETERMINATION OF PETROLEUM COMPONENT BOILING TEMPERATURES

(71) Applicant: Saudi Arabian Oil Company, Dhahran (SA)

(72) Inventors: Hendrik Muller, Dhahran (SA); Frederick M. Adam, Dhahran (SA); Imran Ahmed Naqvi, Khobar North (SA); Radwan Bakor, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 853 days.

(21) Appl. No.: 17/356,142

(22) Filed: Jun. 23, 2021

(65) Prior Publication Data

US 2022/0412903 A1   Dec. 29, 2022

(51) Int. Cl.
*G01N 25/08* (2006.01)
*G01N 33/28* (2006.01)
*G16C 20/70* (2019.01)

(52) U.S. Cl.
CPC ......... *G01N 25/08* (2013.01); *G01N 33/2835* (2013.01); *G16C 20/70* (2019.02)

(58) Field of Classification Search
None
See application file for complete search history.

(56) References Cited

U.S. PATENT DOCUMENTS

| | | | |
|---|---|---|---|
| 7,556,716 B2 | 7/2009 | Burian et al. | |
| 7,598,487 B2 | 10/2009 | Qian et al. | |
| 7,820,015 B2 | 10/2010 | Burian et al. | |
| 8,682,597 B2 | 3/2014 | Brown et al. | |
| 9,665,693 B2 | 5/2017 | Saeger et al. | |
| 2003/0180963 A1 | 9/2003 | Evans et al. | |
| 2007/0050154 A1* | 3/2007 | Albahri | G16C 20/30 702/22 |
| 2007/0114377 A1 | 5/2007 | Qian et al. | |
| 2008/0173804 A1 | 7/2008 | Indo et al. | |
| 2009/0059995 A1 | 3/2009 | Burian et al. | |
| 2010/0204925 A1* | 8/2010 | Albahri | G01N 33/28 702/25 |
| 2014/0107941 A1 | 4/2014 | Albahri | |
| 2015/0107331 A1 | 4/2015 | Wang et al. | |
| 2018/0143168 A1 | 5/2018 | Wang et al. | |

(Continued)

OTHER PUBLICATIONS

Adam et al., "Supercritical fluid chromatography hyphenated with twin comprehensive two-dimensional gas chromatography for ultimate analysis of middle distillates," J. Chromatography A 2010, 1217(8):1386-139, 9 pages.

(Continued)

*Primary Examiner* — Erica S Lin
(74) *Attorney, Agent, or Firm* — Fish & Richardson P.C.

(57) ABSTRACT

Embodiments herein relate to systems and methods for identifying a plurality of components of a petroleum sample. Embodiments further relate to determining respective atmospheric equivalent boiling points (AEBPs) for respective ones of the plurality of components. Embodiments further relate to determining a boiling curve for the petroleum sample based on the respective AEBPs. Embodiments further relate to outputting an indication of the boiling curve for the petroleum sample. Other embodiments may be described or claimed.

20 Claims, 16 Drawing Sheets

(56) References Cited

U.S. PATENT DOCUMENTS

2023/0176018 A1 6/2023 Muller et al.

OTHER PUBLICATIONS

Alawani et al., "Characterization of Crude Oils through Alkyl Chain-Based Separation by Gel Permeation Chromatography and Mass Spectrometry," Energy Fuels, 2020, 34(5):5414-5425, 12 pages.

Beckey, "Field desorption mass spectrometry: A technique for the study of thermally unstable substances of low volatility," Ion Phys. Journal of Mass Spectrometry and Ion Physics, 1969, 2(6):500-503, 3 pages.

Behrenbruch et al., "Classification and characterisation of crude oils based on distillation properties," Journal of Petroleum Science and Engineering 2007, 57(1-2):166-180, 15 pages.

Djokic et al., "Comprehensive Characterization of a Steam Cracking Pyrolysis Fuel Oil using GC × GC-FID and FT-ICR MS," Fuel Processing Technology 2018, 182:15-25, 11 pages.

França et al., "Speciation and quantification of high molecular weight paraffins in Brazilian whole crude oils using high-temperature comprehensive two-dimensional gas chromatography," Fuel 2018, 234:1154-1164, 11 pages.

Gross et al., "Field desorption mass spectrometry of large multiply branched saturated Hydrocarbons," Journal of Mass Spectrometry 2001, 36:522-528, 7 pages.

Hodgkins et al., "Hydrodearylation of Heavy Alkyl-Bridged Noncondensed Alkyl Aromatics to Recover High-Value Mono-Aromatics," Industrial & Engineering Chemistry Research, 2019, 58(41):19042-19049, 8 pages.

Kinney, "A system correlating molecular structure of organic compounds with their boiling points," J. Org. Chem. 1941, 6(2):220-228, 9 pages.

Kinney, "A system correlating molecular structure of organic compounds with their boiling points," J. Am. Chem. Soc., 1938, 60(12):3032-3039, 8 pages.

Kinney, "Calculation of Boiling Points of Aliphatic Hydrocarbons," Ind. Eng. Chem., 1940, 32:559-562.

Kudchadker et al., "Vapor Pressure and Boiling Points of Normal Alkanes, $C_{21}$ to $C_{100}$," Journal of Chemical and Engineering Data, 1966, 11(2):253-255, 3 pages.

Kumar et al., "Mechanistic Kinetic Modeling of the Hydrocracking of Complex Feedstocks, such as Vacuum Gas Oils," Industrial & Engineering Chemistry Research, 2007, 46(18):5881-5897, 17 pages.

Li et al., "Quantitative Molecular Composition of Heavy Petroleum Fractions: A Case Study of FCC Decant Oil," Energy Fuels, Feb. 2020, 26 pages.

Li et al., "Selective methylation of sulfides in petroleum for electrospray ionization mass spectrometry analysis," Energy & Fuels, 2019, 33:1797-1802, 6 pages.

Lopes et al., "Extending the true boiling point curve of a heavy crude oil by means of molecular distillation and characterization of the products obtained," Petroleum Science and Technology, 2017, 35(14):1523-1529, 8 pages.

Lozano et al., "Pushing the analytical limits: new insights into complex mixtures using mass spectra segments of constant ultra-high resolving power," Chemical Science, 2019, 10:6966-6978, 14 pages.

Mahé et al., "Overcoming the high-temperature two-dimensional gas chromatography limits to elute heavy compounds," J. Chromatogr A., 2012, 1229:298-301, 4 pages.

Marshall et al., "Petroleomics: Chemistry of the underworld," Proceedings of the National Academy of Sciences PNAS, 2008, 105(47):18093-18095, 6 pages.

Mennito et al., "Characterization of Heavy Petroleum Saturates by Laser Desorption Silver Cationization and Fourier Transform Ion Cyclotron Resonance Mass Spectrometry," Energy Fuels, 2013, 27(12):7348-7353, 6 pages.

Miquel et al., "A new method for petroleum fractions and crude oil characterization," SPE Reservoir Engineering, May 1992, 7(2):265-270, 6 pages.

Müller et al., "Characterization of high-molecular-weight sulfur-containing aromatics in vacuum residues using Fourier transform ion cyclotron resonance mass spectrometry," Analytical Chemistry, Apr. 2005, 77(8):2536-2543, 8 pages.

Muller et al., "Evaluation of Quantitative Sulfur Speciation in Gas Oils by Fourier Transform Ion Cyclotron Resonance Mass Spectrometry: Validation by Comprehensive Two-Dimensional Gas Chromatography," Journal of the American Society for Mass Spectrometry, Feb. 2012, 23:806- 815, 25 pages.

Muller et al., "Innate Sulfur Compounds as an Internal Standard for Determining Vacuum Gas Oil Compositions by APPI FT-ICR MS," Energy Fuels, Jun. 2020, 34:8260-8273, 52 pages.

Muller et al., "Narrow Distillation Cuts for an Improved Characterization of Crude Oil: An Insight on Heteroatoms in Heavy Fraction Molecules," International J. Oil, Gas and Coal Technology, 2021, 26(1):40-59, 20 pages.

Muller et al., "Saturated Compounds in Heavy Petroleum Fractions," Energy Fuels, 2020, 34:10713-10723, 11 pages.

Ng et al., "Distributions of Aromatics, Nitrogen, and Sulfur in Cracked Liquid Products from Microactivity Tests," Energy & Fuels, 2000, 14(4):945-946, 2 pages.

Potgieter et al., "Analysis of oxidised heavy paraffininc products by high temperature comprehensive two-dimensional gas chromatography," J Chromatogr A, 2017, 1509:123-131, 9 pages.

Purcell et al., "Atmospheric Pressure Photoionization Fourier Transform Ion Cyclotron Resonance Mass Spectrometry for Complex Mixture Analysis," Analytical Chemistry, 2006, 78(16):5906-5912, 7 pages.

Qian et al., "Characterization of large nonvolatile polyaromatic molecules by a combination of in-source pyrolysis and field desorption mass spectrometry," Energy Fuels, 2001, 15(4):949-954, 6 pages.

Qian et al., "Desorption and Ionization of Heavy Petroleum Molecules and Measurement of Molecular Weight Distributions," Energy Fuels, 2007, 21:1042-1047, 6 pages.

Qian et al., "Resolution and Identification of Elemental Compositions for More than 3000 Crude Acids in Heavy Petroleum by Negative-Ion Microelectrospray High Field Fourier Transform Ion Cyclotron Resonance Mass Spectrometry," Energy & Fuels, 2001, 15(6):1505-1511, 7 pages.

Reiter et al., "Characterization of crude oil by real component surrogates," Energy & Fuels, 2014, 28(8):5565-5571, 7 pages.

Revellin et al., "Specific Nitrogen Boiling Point Profiles of Vacuum Gasoils," Energy & Fuels, 2005, 19(6):2438-2444, 7 pages.

Rodgers et al., "Molecular Characterization of Petroporphyrins in Crude Oil by Electrospray Ionization Fourier Transform Ion Cyclotron Resonance Mass Spectrometry," Canadian Journal of Chemistry, 2001, 79:546-551, 6 pages.

Rodgers et al., "Petroleum Analysis," Anal. Chem., 2011, 83(12):4665-4687, 23 pages.

Shearer et al., "Simultaneous measurement of hydrocarbons and sulfur compounds using flame ionization and sulfur chemiluminescence detection for sulfur simulated distillation," Journal of High Resolution Chromatography, 1999, 22(7):386-390, 5 pages.

Vendeuvre et al., "Characterisation of middle-distillates by comprehensive two-dimensional gas chromatography (GC x Gc): A powerful alternative for performing various standard analysis of middle-distillates," Journal of chromatography A, 2005, 1086(1-2):21-28, 8 pages.

Wang et al., "Detailed Chemical Composition of Straight-Run Vacuum Gas Oil and its Distillates as a Function of the Atmospheric Equivalent Boiling Point," Energy Fuels, 2016, 30(2):968-974, 7 pages.

Xavier et al., "On the use of continuous distribution models for characterization of crude oils," Latin American Applied Research, 2011, 41(4):325-329, 5 pages.

Zhou et al., "Characterization of Saturated Hydrocarbons in Vacuum Petroleum Residua: Redox Derivatization Followed by Negative-

(56) References Cited

OTHER PUBLICATIONS

Ion Electrospray Ionization Fourier Transform Ion Cyclotron Resonance Mass Spectrometry," Energy Fuels, 2014, 28(1):417-422, 6 pages.

Akhlaq et al., "Detailed analysis of crude oil group types using reversed-phase high-performance liquid chromatography," Journal of Chromatography A, Aug. 19, 1994, 677(2):265-272, 8 pages.

Akhlaq, "Rapid group-type analysis of crude oils using high-performance liquid chromatography and gas chromatography," Journal of Chromatography A, Aug. 6, 1993, 644(2):253-258, 6 pages.

Alawani et al., "Evaluation of Polycyclic Aromatic Hydrocarbon Removal from Hydrocracking Recycle Streams," Energy & Fuels, Dec. 23, 2019, 34(1):179-187, 9 pages.

Ali et al., "Application of high performance liquid chromatography for hydrocarbon group type analysis of crude oils," Fuel Science & Technology International, 1994, 12(1):21-33, 13 pages.

Ali et al., "Hydrocarbon Group Types Analysis of Petroleum Products: A Comparative Evaluation of HPLC and TLC Analytical Performance," Petroleum Science and Technology, Jan. 2002, 20(7-8):771-782, 12 pages.

Boduszynski, "Composition of Heavy Petroleums. 1. Molecular Weight, Hydrogen Deficiency, and Heteroatom Concentration as a Function of Atmospheric Equivalent Boiling Point up to 1400° F. (760° C.)," Energy Fuels, Jan. 1, 1987, 1:2-11, 10 pages.

cdn.standards.iteh.ai [online], "Standard Test Method for Boiling Point Distribution of Samples with Residues Such as Crude Oils and Atmospheric and Vacuum Residues by High Temperature Gas Chromatography," ASTM-D7169-20, Published on Jun. 2020, originally approved in 2005, retrieved on May 9, 2024, retrieved from URL <https://cdn.standards.iteh.ai/samples/106937/3c9e8ebc45b24532b374dle516f387af/ASTM-D7169-20e1.pdf>, 11 pages.

cdn.standards.iteh.ai [online], "Standard Test Method for Density, Relative Density, and API Gravity of Liquids by Digital Density Meter," ASTM-D4052-22, Published on May 2022, originally approved in 1981, retrieved on May 9, 2024, retrieved from URL <https://cdn.standards.iteh.ai/samples/112378/1e427858c52b4fff89a470b85eeda29d/ASTM-D4052-22.pdf>, 5 pages.

cdn.standards.iteh.ai [online], "Standard Test Method for Detailed Analysis of Petroleum Naphthas through n-Nonane by Capillary Gas Chromatography," ASTM-D5134-21, Published on Dec. 2021, originally approved in 1990, retrieved on May 9, 2024, retrieved from URL <https://cdn.standards.iteh.ai/samples/111381/db3a51clf7b6453b99e66aac6cld5cb3/ASTM-D5134-21.pdf>, 7 pages.

cdn.standards.iteh.ai [online], "Standard Test Method for Determination of Aromatic Hydrocarbon Types in Middle Distillates-High Performance Liquid Chromatography Method with Refractive Index Detection," ASTM-D6591-19, Published Aug. 2019, originally approved in 2000, retrieved on May 9, 2024, retrieved from URL <https://cdn.standards.iteh.ai/samples/103777/54458438be6a43089ca65190ec9df59c/ASTM-D6591-19.pdf>, 6 pages.

cdn.standards.iteh.ai [online], "Standard Test Method for Paraffin, Naphthene, and Aromatic Hydrocarbon Type Analysis in Petroleum Distillates Through 200 by MultiDimensional Gas Chromatography," ASTM-D5443-23, Published Mar. 2023, originally approved in 1993, retrieved on May 9, 2024, retrieved from URL <https://cdn.standards.iteh.ai/samples/114689/c4f0c0c1c8fc4db5a970ba9bea30a670/ASTM-D5443-23.pdf>, 7 pages.

cdn.standards.iteh.ai [online], "Standard Test Method for Sulfur in Petroleum and Petroleum Products by Energy Dispersive X-ray Fluorescence Spectrometry," ASTM-D4294-21, Published Dec. 2021, originally approved in 1983, retrieved on May 9, 2024, retrieved from URL <https://cdn.standards.iteh.ai/samples/111413/04c650321ec24e31b8a92439645fle7b/ASTM-D4294-21.pdf>, 5 pages.

cdn.standards.iteh.ai [online], "Standard Test Methods for Hydrogen Content of Light Distillates, Middle Distillates, Gas Oils, and Residua by Low-Resolution Nuclear Magnetic Resonance Spectroscopy," ASTM-D4808-17, Published Jun. 2017, originally approved in 1988, retrieved on May 9, 2024, retrieved from URL <https://cdn.standards.iteh.ai/samples/97390/5169f72fbe6845febdd355d308943a31/ASTM-D4808-17.pdf>, 2 pages.

Coutinho et al., "Rapid hydrocarbon group-type semi-quantification in crude oils by comprehensive two-dimensional gas chromatography," Fuel, May 15, 2018, 220:379-388, 10 pages.

Fafet et al., "New Developments in Mass Spectrometry for Group-Type Analysis of Petroleum Cuts—First Part: Improving Quantification of Sulphured Aromatic Compounds in Middle Distillates," Oil & Gas Science and Technology—Rev. IFP, Jul.-Aug. 1999, 54(4):439-452, 14 pages.

Fafet et al., "New Developments in Mass Spectrometry for Group-Type Analysis of Petroleum Cuts—Second Part: Development and Validation of a New Inlet System for Heavy Cuts," Oil & Gas Science and Technology—Rev. IFP, Jul.-Aug. 1999, 54(4):453-462, 10 pages.

Felix et al., "Hydrocarbon Groups Type Analysis of Petroleum Products by HPLC on Specific Stationary Phases," Journal of Liquid Chromatography, Aug. 1987, 10(10):2115-2132, 18 pages.

Gallegos et al., "Petroleum group-type analysis by high resolution mass spectrometry," Analytical Chemistry, Dec. 1, 1967, 39(14):1833-1838, 6 pages.

Hannisdal et al., "Group-Type Analysis of Heavy Crude Oils Using Vibrational Spectroscopy in Combination with Multivariate Analysis," Ind. Eng. Chem. Res., Mar. 2, 2005, 44(5):1349-1357, 9 pages.

Hejazi et al., "Determination of the Composition of Fatty Acid Mixtures Using GC × FI-MS: A Comprehensive Two-Dimensional Separation Approach," Analytical Chemistry, Jan. 15, 2009, 81(4):1450-1458, 9 pages.

Lissitsyna et al., "PIONA analysis of kerosene by comprehensive two-dimensional gas chromatography coupled to time of flight mass spectrometry," Fuel, Jan. 15, 2014, 116:716-722, 7 pages.

Matt et al., "Planar chromatography for the hydrocarbon group type analysis of petroleum middle distillates and coal-derived products," Fuel Processing Technology, Jun. 20, 2002, 77-78:245-253, 9 pages.

Mitschke et al., "Comprehensive Gas Chromatography-Time-of-Flight Mass Spectrometry Using Soft and Selective Photoionization Techniques," Analytical Chemistry, Jul. 28, 2006, 78(18):6364-6375, 12 pages.

Peterson, "Mass Spectrometer All-Glass Heated Inlet," Analytical Chemistry, Dec. 1, 1962, 34(13):1850-1851, 2 pages.

Qian et al., "Deducing molecular compositions of petroleum products using GC-field ionization high resolution time of flight mass spectrometry," International Journal of Mass Spectrometry, Sep. 1, 2007, 265(2-3):230-236, 7 pages.

Qiang et al., "Hydrocarbon group-type analysis of high boiling petroleum distillates by HPLC," Journal of Petroleum Science and Engineering, Jan. 1999, 22(1-3):31-36, 6 pages.

Roussis et al., "Hydrocarbon Compound Type Analysis by Mass Spectrometry: On the Replacement of the All-Glass Heated Inlet System with a Gas Chromatograph," Energy & Fuels, Jan. 25, 2001, 15(2):477-486, 10 pages.

Stafford et al., "A mass spectrometer all-glass heated inlet," International Journal of Mass Spectrometry and Ion Physics, Apr. 1968, 1(1):87-92, 6 pages.

Striebich et al., "Hydrocarbon Group-Type Analysis of Petroleum-Derived and Synthetic Fuels Using Two-Dimensional Gas Chromatography," Energy & Fuels, Aug. 21, 2014, 28(9):5696-5706, 11 pages.

International Search Report and Written Opinion in International Appln. No. PCT/US2024/047239, mailed on Nov. 27, 2024, 13 pages.

Adam et al., "Towards Comprehensive Hydrocarbons Analysis of Middle Distillates by LC-GCxGC," Journal of Chromatographic Science, Nov./Dec. 2007, 45:643-649, 7 pages.

\* cited by examiner

710

| NR | AR | C | DBE | FID | AEBP |
|---|---|---|---|---|---|
| 0 | 0 | 6 | 0 | 0.00% | 63.4 |
| 0 | 0 | 7 | 0 | 0.00% | 99.8 |
| 0 | 0 | 8 | 0 | 0.00% | 131.4 |
| 0 | 0 | 9 | 0 | 0.02% | 159.2 |
| 0 | 0 | 10 | 0 | 0.08% | 184.1 |
| 0 | 0 | 11 | 0 | 0.13% | 206.7 |
| 0 | 0 | 12 | 0 | 0.18% | 227.2 |
| 0 | 0 | 13 | 0 | 0.29% | 246.2 |
| 0 | 0 | 14 | 0 | 0.83% | 263.7 |
| 0 | 0 | 15 | 0 | 1.10% | 280.0 |
| 0 | 0 | 16 | 0 | 1.32% | 295.3 |
| 0 | 0 | 17 | 0 | 1.45% | 309.6 |
| 0 | 0 | 18 | 0 | 1.60% | 323.1 |
| 0 | 0 | 19 | 0 | 1.37% | 335.9 |
| 0 | 0 | 20 | 0 | 1.39% | 348.0 |
| 0 | 0 | 21 | 0 | 1.28% | 359.6 |
| 0 | 0 | 22 | 0 | 0.98% | 370.6 |
| 1 | 0 | 9 | 1 | 0.00% | 166.7 |
| 1 | 0 | 10 | 1 | 0.03% | 191.7 |
| 1 | 0 | 11 | 1 | 0.06% | 214.2 |
| 1 | 0 | 12 | 1 | 0.09% | 234.8 |
| 1 | 0 | 13 | 1 | 0.19% | 253.7 |
| 1 | 0 | 14 | 1 | 0.29% | 271.2 |
| 1 | 0 | 15 | 1 | 0.48% | 287.5 |
| 1 | 0 | 16 | 1 | 0.76% | 302.8 |
| 1 | 0 | 17 | 1 | 0.69% | 317.1 |
| 1 | 0 | 18 | 1 | 0.59% | 330.6 |
| 1 | 0 | 19 | 1 | 0.76% | 343.4 |
| 1 | 0 | 20 | 1 | 0.47% | 355.5 |
| 1 | 0 | 21 | 1 | 0.60% | 367.1 |
| 1 | 0 | 22 | 1 | 0.55% | 378.1 |
| 2 | 0 | 10 | 2 | 0.00% | 197.7 |
| 2 | 0 | 11 | 2 | 0.02% | 220.2 |
| 2 | 0 | 12 | 2 | 0.05% | 240.8 |
| 2 | 0 | 13 | 2 | 0.04% | 259.7 |
| 2 | 0 | 14 | 2 | 0.09% | 277.2 |
| 0 | 1 | 6 | 4 | 0.00% | 84.4 |
| 0 | 1 | 7 | 4 | 0.01% | 120.9 |
| 0 | 1 | 8 | 4 | 0.07% | 152.4 |
| 0 | 1 | 9 | 4 | 0.87% | 180.3 |
| 0 | 1 | 10 | 4 | 0.98% | 205.2 |
| 0 | 1 | 11 | 4 | 1.16% | 227.7 |
| 0 | 1 | 12 | 4 | 0.52% | 248.3 |
| 0 | 1 | 13 | 4 | 0.61% | 267.2 |
| 0 | 1 | 14 | 4 | 0.61% | 284.8 |
| 0 | 1 | 15 | 4 | 0.55% | 301.1 |
| 0 | 1 | 16 | 4 | 0.49% | 316.3 |
| 0 | 1 | 17 | 4 | 0.48% | 330.7 | continued..

715

| AEBP | CUMULATIVE |
|---|---|
| 63.4 | 0.00% |
| 84.4 | 0.00% |
| 99.8 | 0.00% |
| 120.9 | 0.01% |
| 131.4 | 0.01% |
| 152.4 | 0.08% |
| 159.2 | 0.10% |
| 166.7 | 0.10% |
| 180.3 | 0.97% |
| 181.8 | 1.07% |
| 181.8 | 1.07% |
| 184.1 | 1.15% |
| 191.7 | 1.18% |
| 197.7 | 1.19% |
| 205.2 | 2.17% |
| 205.2 | 2.98% |
| 206.7 | 3.10% |
| 206.7 | 3.74% |
| 206.7 | 3.92% |
| 214.2 | 3.98% |
| 220.2 | 4.00% |
| 227.2 | 4.18% |
| 227.7 | 5.34% |
| 227.8 | 10.37% |
| 229.2 | 11.28% |
| 229.3 | 11.64% |
| 234.8 | 11.73% |
| 240.8 | 11.78% |
| 240.8 | 12.18% |
| 245.3 | 12.75% |
| 246.2 | 13.04% |
| 248.3 | 13.56% |
| 248.3 | 25.36% |
| 249.8 | 26.94% |
| 249.8 | 27.14% |
| 253.7 | 27.33% |
| 259.7 | 27.37% |
| 259.8 | 28.61% |
| 263.7 | 29.44% |
| 264.3 | 32.25% |
| 267.2 | 32.87% |
| 267.3 | 42.54% |
| 268.7 | 43.71% |
| 271.2 | 44.00% |
| 277.2 | 44.09% |
| 277.3 | 45.60% |
| 280.0 | 46.69% |
| 281.8 | 50.04% | continued..

FIG. 7B

DETERMINATION OF PETROLEUM COMPONENT BOILING TEMPERATURES

TECHNICAL FIELD

The present disclosure applies to the determination of boiling temperature(s) of components of a petroleum sample.

BACKGROUND

Development and optimization of oil and gas downstream processes may benefit from knowing the feedstocks, intermediates, and products of the petroleum samples, as well as their chemical transformations at the level of individual molecules. Such detailed knowledge may enable "molecular refining" tailored to the exact chemical composition of the feedstock and product slates. However, on the one hand, determining quantitatively the required molecular information may be challenging, because various speciation techniques with sufficient resolution may have known, and unknown, bias and limitations. On the other hand, the quantitative measurement of bulk properties is routine today. As such a bulk parameter, boiling curves may be considered important for the characterization of petroleum crude oil and fractions, intermediates, and products thereof.

SUMMARY

The present disclosure relates to techniques for the determination of the boiling curve of petroleum samples through a boiling temperature model of individual petroleum components, based on molecular parameters obtained using one or more analytical characterization techniques.

The molecular parameters to build the boiling temperature model include the double bond equivalent (DBE), carbon number, and heteroatom type and content (class) of each component obtained from analysis through, for example, high-, and ultrahigh resolution mass spectrometry (MS) or gas chromatography (GC) such as two-dimensional GC (referred to herein as GC×GC).

The mathematical model allows calculation of the individual atmospheric equivalent boiling points (AEBP) for each identified molecular component. The individual AEBPs are summed to derive the cumulative boiling curve for the entire sample. Embodiments may further include the comparison of such boiling curves calculated from molecular parameters, including elemental formulae obtained using one or more characterization techniques such as ultrahigh resolution MS and GC, with boiling curves obtained through simulated distillation measurements. Embodiments may be applicable to a wide range of petroleum samples, including petroleum crude oils and high- and non-boiling petroleum fractions and refining products such as, but not limited to, vacuum gas oils, atmospheric residues, vacuum residues, and asphaltenes, mid and high boiling products of cracking, hydrocracking, hydrotreating processes, and pyrolysis products.

In some implementations, a computer-implemented method includes identifying, by an electronic device, a plurality of components of a petroleum sample; determining, by the electronic device, respective AEBPs for respective ones of the plurality of components; determining, by the electronic device, a boiling curve for the petroleum sample based on the respective AEBPs; and outputting, by the electronic device, an indication of the boiling curve for the petroleum sample.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method/ the instructions stored on the non-transitory, computer-readable medium.

The subject matter described in this specification can be implemented in particular implementations, to realize one or more advantages. For example, the claimed technique may establish a direct relation between the boiling point of the characterized sample, including petroleum crude oils and fractions, intermediates, and products thereof, and detailed composition data obtained of the sample using advanced analytical techniques. In some embodiments, the obtained boiling information of individual components is combined to calculate the boiling curve of the sample. The boiling curves that are obtained in accordance with embodiments herein may be compared directly and quantitatively with the boiling curves established through true boiling point (TBP) distillation and/or simulated distillation (SIMDIS), both of which are internationally established parameters used for the characterization of petroleum samples. The match between the TBP or SIMDIS boiling curves and the boiling curve(s) calculated herein may allow for the comparison of semi-quantitative results obtained using analytical techniques such as GC×GC or MS. Embodiments may also establish a validated quantitative link between advanced heavy ends speciation by Fourier-transform ion cyclotron resonance mass spectrometry (FT-ICR MS) with a real-world property such as the global boiling distribution of the sample. As a result, embodiments herein allow for updated quantitative analytical capabilities: For example, embodiments allow one to compare data from previously complementary techniques (e.g., FT-ICR MS and SIMDIS). Additionally, embodiments allow for a determination of whether a speciation measurement covers the sample composition in its entirety, or only a part of the sample composition. Such a determination may be important for techniques with unknown, or previously unquantifiable biases. For instance, allow for a determination of the extent to which an ultrahigh-resolution mass spectrometry measurement describes a sample's composition, or the amount of undetected high boiling components identified through a GC×GC analysis.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

FIGS. 7A, 7B, and 7C collectively depict an example of modeling a boiling curve of a petroleum sample based on the boiling temperatures of the various components of the sample, in accordance with various embodiments.

Like reference numbers and designations in the various drawings indicate like elements.

DETAILED DESCRIPTION

The following detailed description describes techniques for generating a modeled boiling curve of a petroleum sample, in accordance with various embodiments. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

As previously noted, boiling curves may be considered important parameters for the characterization of petroleum crude oil and fractions, intermediates, and products thereof (collectively referred to herein as a petroleum sample). Techniques such as SIMDIS may be used to approximate true boiling behavior of a petroleum sample through actual distillation, and may be used in accordance to several international standard tests related to, for example, crude assays, refining yield prediction and optimization, and downstream process management, as well as process development. Commercial software tools may translate SIMDIS data into true boiling curves, and vice versa.

More generally, SIMDIS may involve GC-based evaporation and elution of the sample constituents with limited chromatographic resolution, where the retention time is correlated with the boiling point. Various SIMDIS-related techniques exist for light, intermediate and heavy (i.e., high boiling) samples, which may require high-temperature (HT) techniques or equipment. The recovery of the heaviest samples may be captured by an internal standard, and non-recoverable material constitutes typically around 5-20 percent by weight (wt %) for crude oils. Higher boiling and non-boiling petroleum samples, which may be referred to as "heavy ends", such as vacuum residue factions are not as volatile, and may exhibit poor SIMDIS recoveries.

Because the boiling characteristics for component groups of different polarity, such as paraffins and condensed aromatic molecules, may deviate in the GC retention behavior, the boiling point-GC correlation depends on an estimation of the sample composition. The composition may be determined by a range of state-of-the-art analytical techniques, depending on the sample type.

Figure 1A:
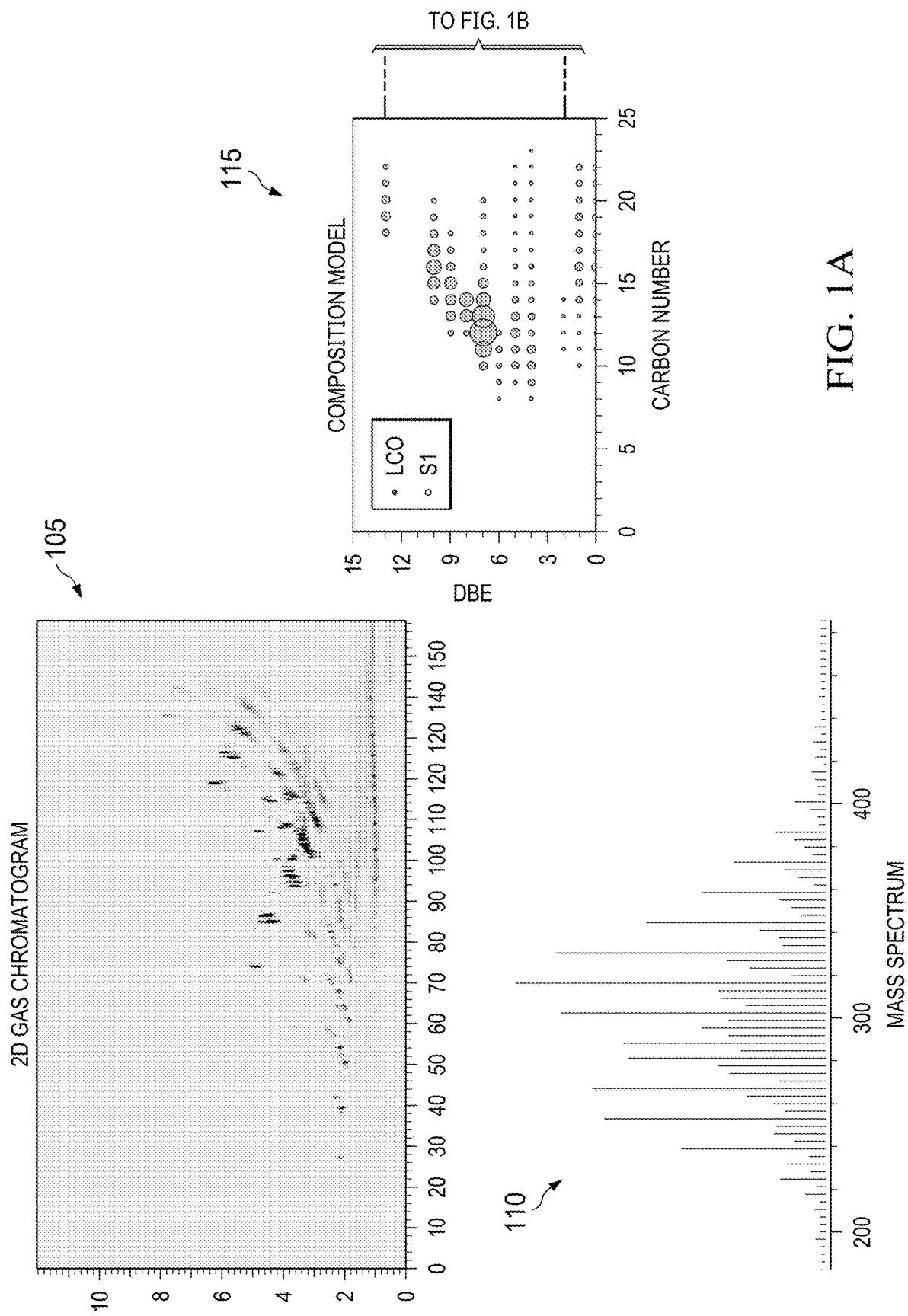
FIGS. 1A and 1B collectively depict an example schematic overview of the technique of modeling a boiling curve of a petroleum sample, in accordance with various embodiments.
Figure 1B:
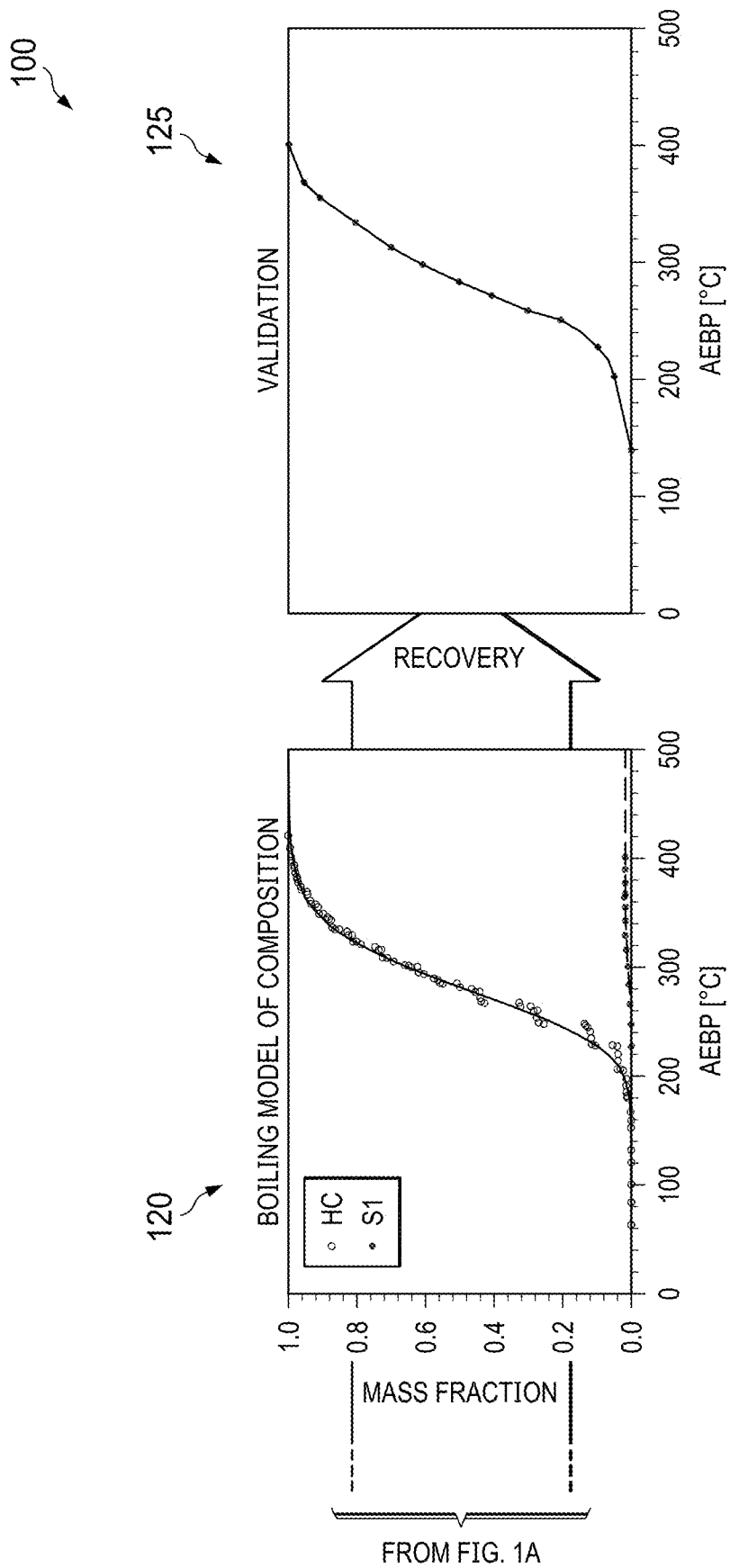

FIGS. 1A and 1B collectively depict an example schematic overview 100 of the technique of modeling a boiling curve of a petroleum sample, in accordance with various embodiments. Characterization data related to the petroleum sample is generated at 105 or 110. For example, the characterization data may be based on GC×GC at 105, mass spectrometry at 110, or both. Generally, the characterization data may be used to identify different components of the petroleum sample, as will be discussed in detail below.

Based on the characterization data from 105 or 110, a composition model may be generated at 115. For example, the X-axis of the composition model 115 depicts increasing carbon number, while the Y-axis depicts increasing DBE. Such information may be available for various compound classes, including pure hydrocarbon and heteroatom containing compounds. Generally, the composition model at 115 may provide an indication of the different components of the petroleum sample. An AEBP for the petroleum sample may then be calculated for each element of the composition model 115. The AEBP of each component may then be used to generate a cumulative boiling curve of the petroleum sample as shown at 120. The boiling curve calculated at 120 may then be validated at 125, for example through comparison with a SIMDIS-generated curve.

Analytical Techniques for Gas Chromatography Based Simulated Distillation

SIMDIS by GC flame-ionization detection (FID) may be used to determine the boiling range for petroleum samples containing molecules that have between five carbon atoms (C5) and 100 carbon atoms (C100), as well as residue molecules with more than 100 carbon atoms (C100+). Data obtained with GC-based techniques, such as GC×GC, may also be related to the boiling point of the components using established compound group specific correlations. This technique may therefore have the advantage of availing detailed speciation of middle distillates and even light vacuum gas oil (VGO) samples in addition to the boiling curve, enabling the creation of compound family specific boiling curves.

The use of sulfur and nitrogen selective detectors, such as sulfur chemiluminescence (SCD) and nitrogen chemiluminescence detection (NCD), may avail the boiling distributions of heteroatom components in petroleum crude oils and fractions up to VGO cuts.

Analytical Techniques for Detailed Speciation

For low boiling fractions of the petroleum sample (which may also be referred to as "light ends"), quantitative knowledge of the composition may be obtainable through GC-based detailed hydrocarbon analysis (DHA), and the quantitative knowledge of the individual components may be translated into boiling curves through commercial software tools. The composition of lighter components of the petroleum sample, as measured in terms of percentage of mass of the petroleum sample (mass %), may be identified by applying a back-flush GC FID technique. Such lighter components may include, for example, components of the petroleum sample that include between one carbon atom (C1) per molecule to nine carbon atoms (C9) per molecule. In this technique, components with more than nine carbon atoms per molecule (C9+) may be vented through the back-flush valve.

Heavy petroleum fractions, for example VGO or vacuum residue (VR) samples, and heavy crude oils may be speciated by high-resolution mass spectrometry, commonly through qualitative or semi-quantitative analysis. As used herein, high-resolution mass spectrometry refers to spectrometry with a resolution that is sufficient to identify the underlying elemental formulae associated with one or more mass signals. In some embodiments, the resolution (as identified based on peak width at half-peak height) may be approximately 2,000. In other embodiments, the resolution may be greater such as approximately 400,000, 1,000,000, or more. Typically, the mass spectral resolution may be based on factors such as the complexity of the sample composition where samples with increasing hetero atom content or increasing molecular weight compounds may include greater resolutions.

Typical techniques for petroleum component ionization may include electrospray ionization (ESI) and atmospheric pressure photoionization (APPI), and less frequently chemical derivatization, or addition of dopants for selective analysis. Some studies have also explored direct quantitative applications of ultrahigh resolution mass spectrometry for selected component groups in petroleum samples.

Saturated compounds may be difficult to ionize, as they may undergo fragmentation in most common techniques. Various approaches have been reported for the detailed characterization of heavy petroleum saturates compounds. Such approaches may include mass spectrometry with direct ionization or after derivatization, high temperature gas chromatography, and molecular modeling. Field desorption (FD) may be used as a soft ionization technique for thermally unstable substances in MS. In some embodiments, FD-MS may be used for the analysis of large multiply branched saturated hydrocarbons with up to more than 100 carbon atoms, heavy polyaromatic compounds, or molecular weight distributions of saturated and heavy petroleum components. In some embodiments, saturated HCs in VR petroleum fractions may be converted, through ruthenium-ion-catalyzed oxidation (RICO), into ketones. The ketones may then be reduced to alcohols that may be analyzed using ESI FT-ICR MS. Alternatively, heavy petroleum saturates may be characterized by silver cation assisted laser desorption ionization (Ag+LDI) coupled with FT-ICR MS. High temperature (HT) GC and HT GC×GC may be applied to determine the saturated compounds. In some embodiments, chromatographic separation may enable the detection of normal and isoparaffins, and some naphthenic compounds in crude oils. In some embodiments, FD-MS, using a commercial high-resolution time of flight mass analyzer, may be used to characterize hydrocarbon species in separated saturates fractions.

The analytical techniques described above may produce a description of the sample composition that encompasses the following attributes for each sample component: the number and type of heteroatoms, such as the number of sulfur, nitrogen, and oxygen atoms, the number of carbon atoms, and the number of hydrogen atoms relative to the carbon and hetero atoms, expressed as a DBE value following equation 1, with carbon, hydrogen and nitrogen referring to the number of the respective atoms in each molecular component:

$$DBE = \text{Carbon} - \text{Hydrogen}/2 + \text{Nitrogen}/2 + 1 \quad [\text{Equation 1}]$$

Boiling Point Model

The AEBP of individual molecular parameters of a petroleum sample may be calculated using an empirical model combining three components; a carbon number dependent part), combined with a DBE dependent term (A=DBE-term), and a sulfur atom and DBE co-dependent part (B=S-term) shown in equation 2.

This model may simplify the required molecular parameter input by omission of structural details, such as alkyl branching, aromatic ring configuration, alkyl substitution pattern etc., to focus on readily available information obtained through state-of-the-art analytical measurements.

$$AEBP = 236.45 \times \ln(C\# + A_{(S\#,DBE)}) - 360.31 + B_{(DBE)} \quad [\text{Equation 2}]$$

In Equation 2, A, and B may depend on the number of sulfur atoms (S #) and DBE value in the component under analysis, as defined in equations 3, 4, and 4a, below:

$$A = (-0.1447 \times DBE + 3.7578) \times S\# \quad [\text{Equation 3}]$$

If DBE is less than 10, then:

$$B_{(DBE<10)} = -0.751 \times DBE + 8.270 \quad [\text{Equation 4}]$$

Otherwise, if DBE greater than, or equal to, 10, then:

$$B_{(DBE \geq 10)} = -0.00565 \times DBE^2 + 0.583 \times DBE - 2.720 \quad [\text{Equation 4a}]$$

The model may allow for the estimation of the AEBP for components of the petroleum sample that are typically obtained using analytical speciation techniques (e.g., MS, GC×GC, etc.).

Figure 2:
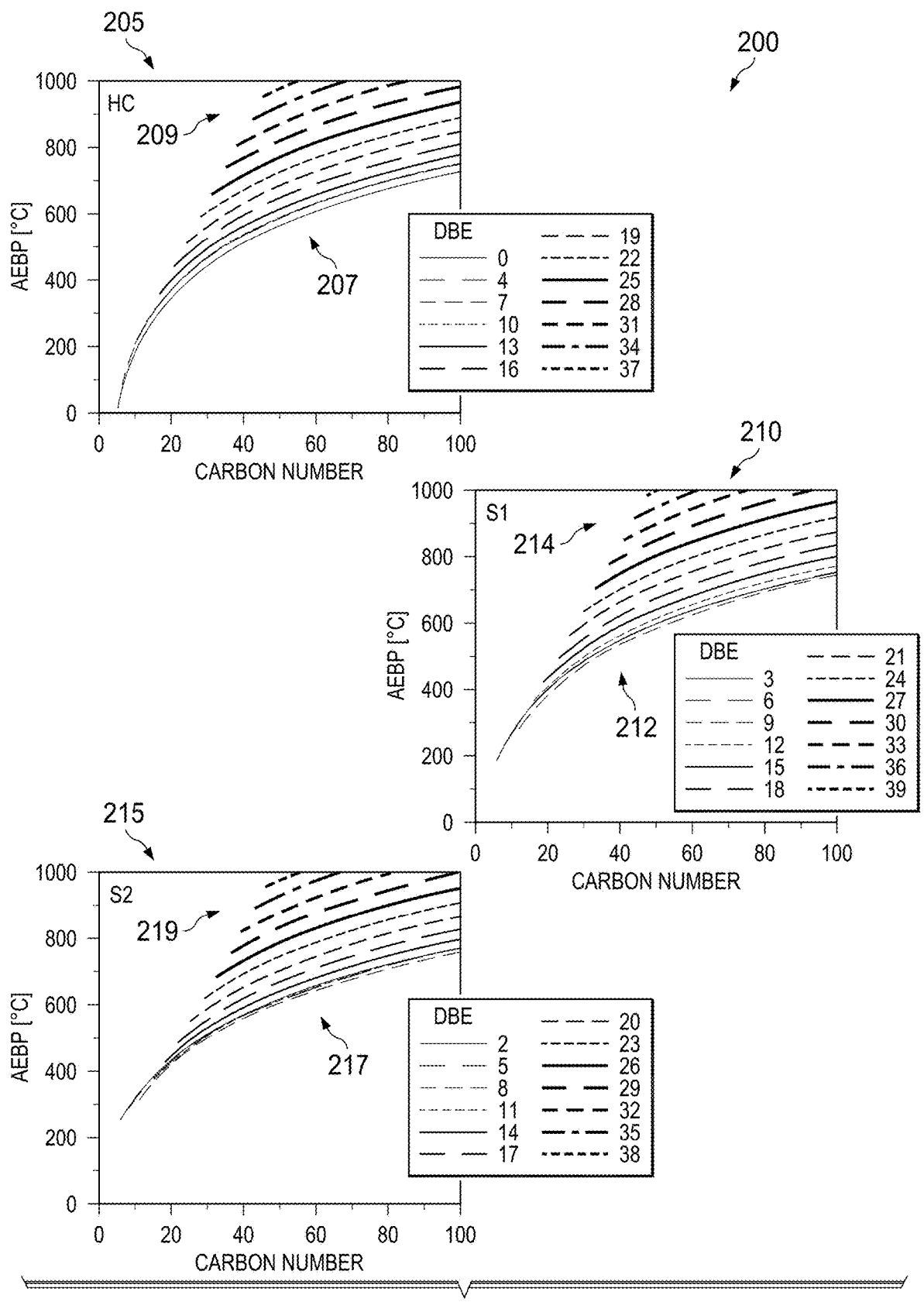
FIG. 2 depicts example AEBP curves for various DBE series hydrocarbon (HC), mono-sulfur (S1), and disulfur (S2) compounds.

FIG. 2 depicts example AEBP curves 200 for various DBE series HC 205, S1 210, and S2 215 compounds. Specifically, FIG. 2 depicts boiling curves for the typical compound families for n-alkanes (HC DBE=0), alkyl aromatic compounds (HC DBE=4) and catacondensed aromatic structures (benzologue series).

Generally, as can be seen in the AEBP curves 200, the AEBP increases as the HC compounds at 205 move from a lower DBE at 207 to a higher DBE at 209. Similarly, the AEBP increases as the S1 compounds 210 move from a lower DBE at 212 to a higher DBE at 214. Finally, the AEBP increases as the S2 compounds move from a lower DBE at 217 to a higher DBE at 219.

As described in further detail below with respect to FIGS. 7A, 7B, and 7C, the boiling curve of the samples may be obtained by detailed characterization of a sample using GC×GC, MS, or some other technique, and then calculating the AEBP for each identified component. The components may then be sorted by their AEBP, and the boiling curve may be generated by calculating the summed abundance with increasing AEBP Details of this technique may be further provided below with respect to, for example, FIGS. 7A, 7B, and 7C.

Analytical Characterization to Obtain Composition Information

As previously noted, composition information may be obtained from separation tools that are capable of speciating heavy petroleum samples. Such tools may be or include, for example, GC, GC×GC, high-resolution MS, ultrahigh-resolution MS, or some other tools. Specific experimental conditions related to various embodiments are described in the following sections.

Comprehensive Two-Dimensional Gas Chromatography (GC×GC)

GC×GC may be a qualitative or semi-quantitative technique used for the determination of HC group types (by aromatic ring families) and sulfur speciation in middle distillates and heavy distillate cuts. As one example, GC×GC may be performed with the following parameters:

The sample may be injected in a split/splitless injector at 310 degrees Celsius (° C.) at a suitable split ratio of 200/1. The column configuration may be: 1st DB1, 15 meters (m)×250 micrometers (μm)×0.25 μm, and 2nd SolgelWax, 1.7 m×100 millimeters (mm)×0.10 μm. As used herein, it will be understood that DB1 and SolgelWax are capillary column types. The single loop modulation may be set to 12 seconds (s). Helium may be used as carrier gas with a constant flow of 0.9 mL/min, and the oven may be started a 50° C. and ramped to 280° C. at 2 degrees Celsius per minute (° C./min). The FID may be operated at 310° C. and 200 hertz (Hz) with standard parameters.

Another GC may be operated with an SCD. The sample may be injected in cool on-column type, heated from 90° C. to 300° C. at 50° C./min. The column configuration may be: 1st DB1-HT, 10 m×320 μm×0.1 μm, and 2nd BPX50, 1.1 m×100 mm×0.10 μm. As used herein, BPX50 refers to a polar stationary phase. The single loop modulation may be set to a period of 20 s. Helium may be used as a carrier gas at a constant flow rate of 1.3 mL/min. The SCD may be operated at 50 Hz, the SCD furnace may be set to 800° C., 02 to 62 mL/min, and H2 to 42 mL/min, and the pressure to 360 torr.

Data processing and GC imaging may then be performed. The identification of compounds may be based on standard compound and literature-reported retention times. Quantification may be achieved by normalization of the chromatogram to the total chromatogram area.

Photoionization High-Resolution MS

MS may be considered a qualitative or semi-quantitative technique for the speciation of components of a petroleum sample. In embodiments where MS is desired, one example may be to perform atmospheric pressure photoionization (APPI) FT-ICR MS. Briefly, a Fourier-transform ion cyclotron resonance mass spectrometer may be used with an APPI source, operated in the positive polarity mode. In one specific and non-limiting example, samples may be dissolved in toluene and diluted to a final concentration of 10 micrograms per milliliter (μg/mL) for the FT-ICR MS measurements. Ion transfer parameters may be tuned based on prior analysis of the sample using a time of flight MS by visually matching the mass signal distributions as described before. Some parameters for this work may be ion accumulated in the collision cell for 0.1 s before transfer to the ICR cell for high-resolution mass measurement. The ion funnel radiofrequency (RF) voltage may be tuned between approximately 80 Volt (V) and approximately 190 V, and may be, for example, approximately 110 V. Ion transfer time may be between approximately 0.8 ms and approximately 1.6 ms for each experiment, and may be, for example, approximately 1.1 ms for lighter cuts and up to approximately 1.4 ms for the heavy samples. 128 scans with four million data points may be recorded and processed. In some embodiments, only radical cations [M+] as the most representative ion species, and their 13-carbon atom (13C) and 34-sulfur atom (34S) isotope signals may be considered.

Field Desorption Mass Spectrometry

To determine the saturated compounds, FD-MS may be used. In one example of FD-MS, the saturated compounds in selected petroleum samples may be separated on alumina by elution with pentane, and then characterized with FD-MS using a time of flight MS with an FD ion source. In one specific and non-limiting example, the emitter may be kept at 10 kilo Volt (kV) and extraction electrodes at 2.4 kV. The ion extraction may be tuned using acetone as reference before the measurement, and the instrument calibrated and performance checked using a polyethylene glycol 1000 (PEG1000) solution in toluene. Standard and samples may then be diluted to 1 mg/mL in toluene and carefully adsorbed onto a field desorption/field ionization (FD/FI) emitter that is mounted on the FD probe. The loaded probe may then be transferred swiftly into the ion source, and the analysis may be started by ramping the emitter current from 0 milliamps (mA) to 40 mA at a rate of 12.8 milliamps per minute (mA/min). Ions were recorded from 35 m/z to 1,600 m/z for 3.2 minutes (200 s). Mass spectra may be obtained by averaging spectra over the time interval during which ions were generated.

After mass recalibration, the centroid mass list may be processed for peak identification. For each mass signal, the Kendrick mass defect (KMD) and modulo 14 may be calculated, and the signals assigned against tabulated values for HC class DBE series. The 13C isotope signals [M+1] that match the theoretical abundance may be added to each compound's abundance.

EXAMPLES

The following provides a number of examples of the above-described techniques. In general, embodiments are described with respect to FIGS. 3-6.

Figure 3:
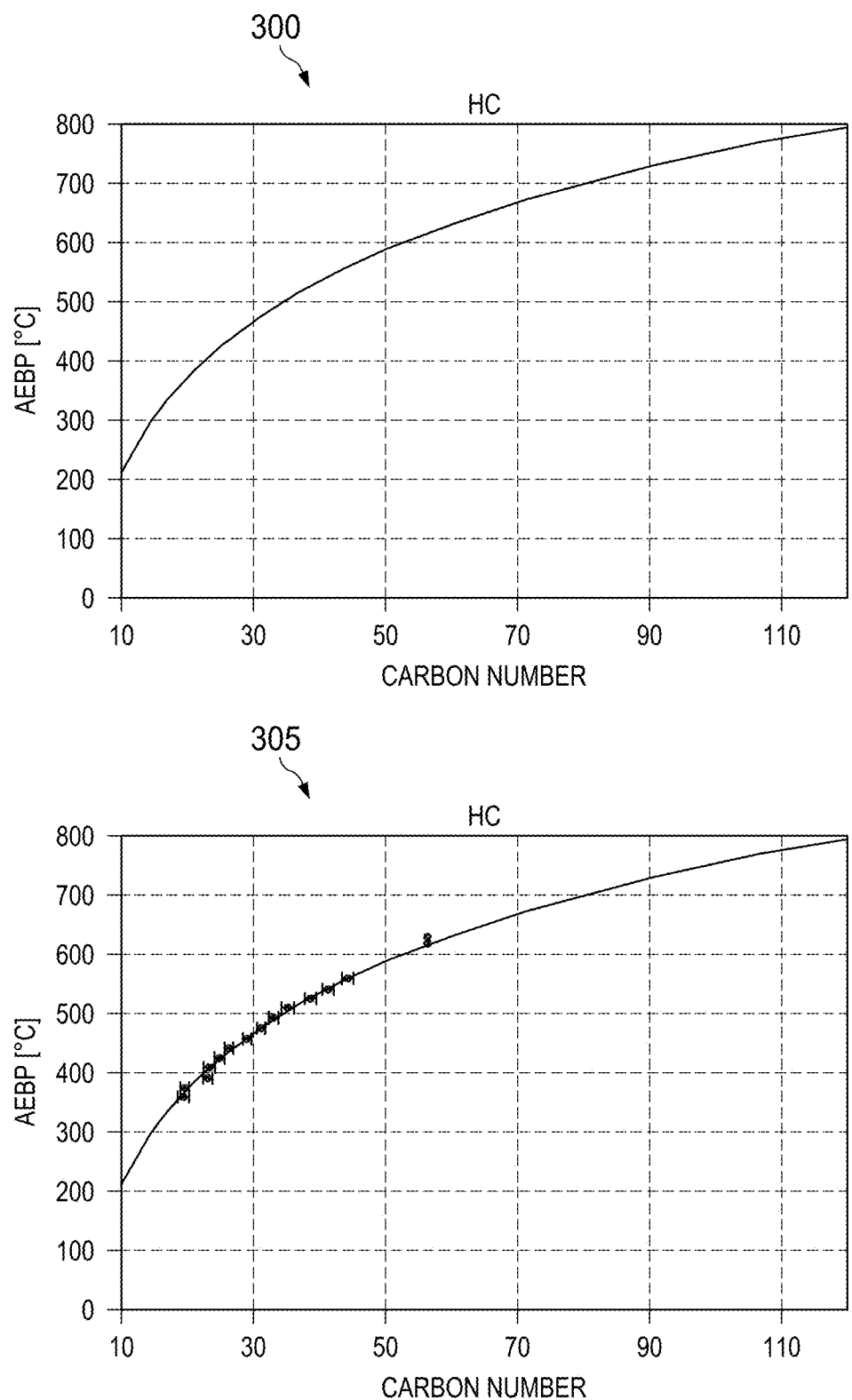
FIG. 3 depicts an example of boiling temperature dependency from carbon number for alkylbenzenes, in accordance with various embodiments.

FIG. 3 depicts an example of boiling temperature dependency from carbon number for alkylbenzenes, in accordance with various embodiments. Specifically, FIG. 3 depicts an example of the boiling temperature dependency from carbon number for alkylbenzenes at 300. FIG. 3 further depicts a comparison of calculated and measured boiling temperatures of alkylbenzenes at 305.

Figure 4:
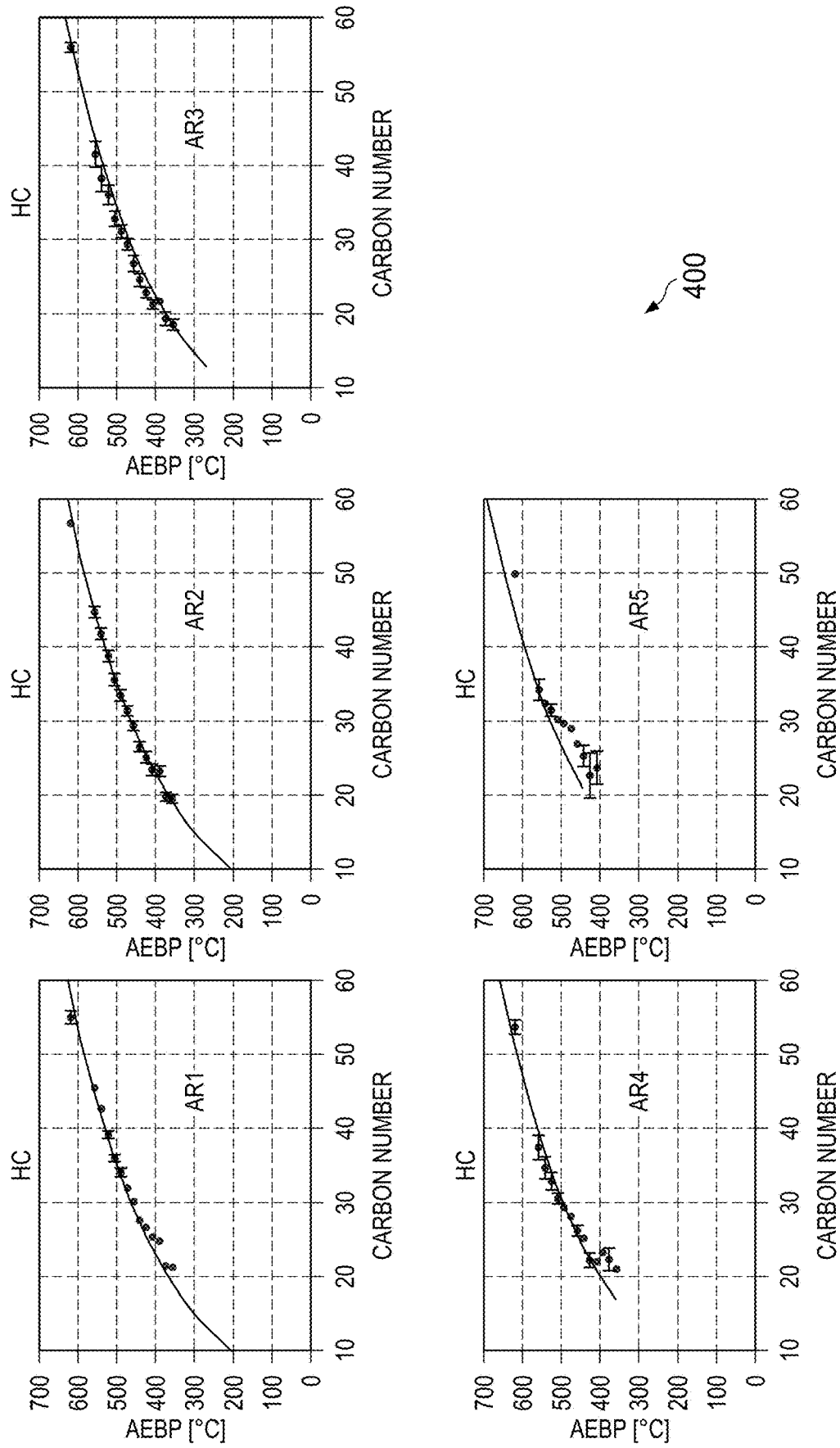
FIG. 4 depicts an example of modeled and measured boiling temperatures of aromatic HC components from straight run distillate fractions, in accordance with various embodiments.

FIG. 4 depicts an example 400 of modeled and measured boiling temperatures of the average aromatic HC components in a series of straight run distillate fractions, in accordance with various embodiments. Specifically, FIG. 4 depicts modeled and measured boiling temperatures of average aromatic HC components with increasing numbers of aromatic rings (ARs). For example, FIG. 4 depicts an HC with one AR (AR1), an HC with two ARs (AR2), an HC with three ARs (AR3), an HC with four ARs (AR4), and an HC with five ARs (AR5).

Figure 5:
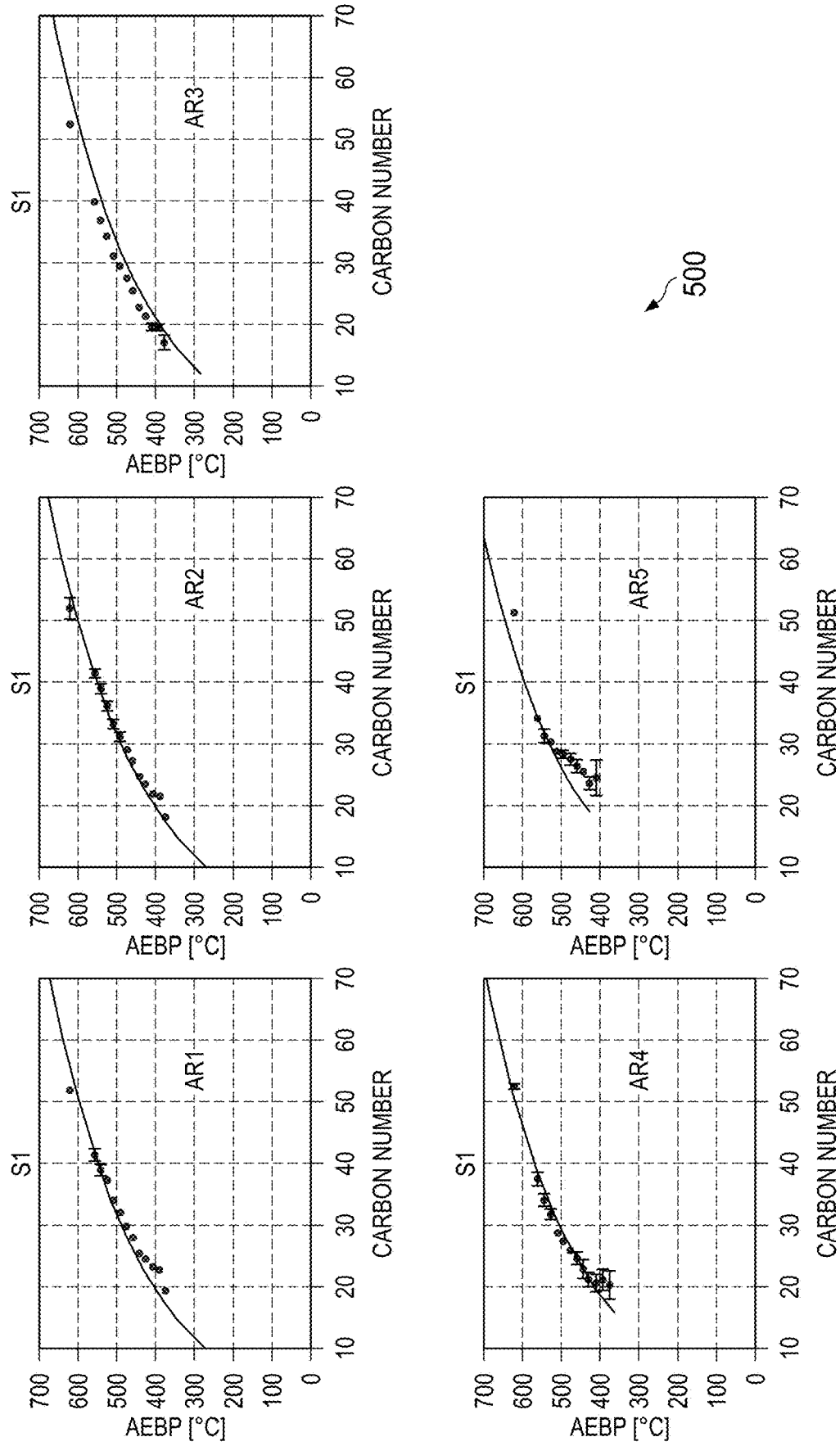
FIG. 5 depicts an example of modeled and measured boiling temperatures of S1 components from straight run distillate fractions, in accordance with various embodiments.

FIG. 5 depicts an example 500 of modeled and measured boiling temperatures of the average aromatic S1 components in a series of straight run distillate fractions, in accordance with various embodiments. Similarly to FIG. 4, FIG. 5 depicts modeled and measured boiling temperatures of the average S1 components with increasing numbers of ARs.

Figure 6:
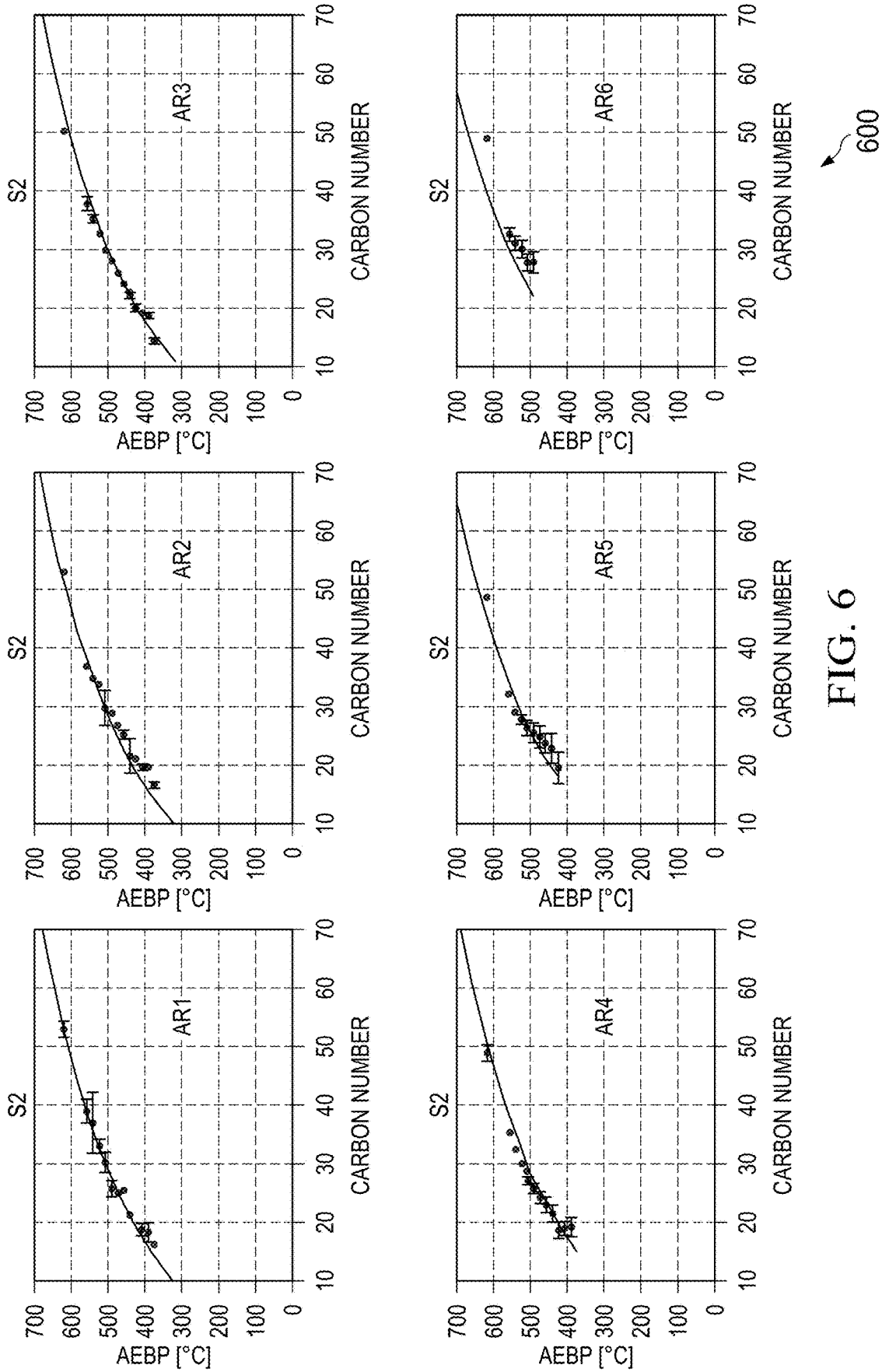
FIG. 6 depicts an example of modeled and measured boiling temperatures of S2 components from straight run distillate fractions, in accordance with various embodiments.

FIG. 6 depicts an example 600 of modeled and measured boiling temperatures of average S2 components in a series of straight run distillate fractions, in accordance with various embodiments. Similarly to FIGS. 4 and 5, FIG. 6 depicts modeled and measured boiling temperatures of the average S2 components with increasing numbers of ARs.

In these examples, a series of straight run distillations fractions with narrow boiling range, in the further text referred to as 'cuts', were obtained and characterized in detail using bulk methods, and semi quantitatively by MS using the innate sulfur compounds as internal standards. The average boiling point of each cut was determined through the distillation process (i.e. the average atmospheric pressure equivalent boiling temperature at which the cut was obtained). The average boiling point and boiling range was confirmed with simulated distillation (SIMDIS). The molecular composition was obtained using GC×GC for the middle distillate cuts and MS for the high boiling cuts and the VR. Both techniques were applied with good agreement for a range of intermediate cuts. The average carbon numbers are thus determined for each AR family in each cut.

As shown in FIG. 3, these data together (i.e., the average AEBP of each cut and the average carbon number of each AR family) show the validity of the model. Aromatic HC compound data for mono-di, tri, tetra, and in parts penta-aromatic families overall fits the predicted boiling curves, as shown in FIG. 4. The standard deviation for average carbon numbers are obtained for the for the parent family without naphthenic ring, and with one and two naphthenic rings (e.g., DBE 4, 5, and 6 for benzenes, naphthenobenzenes, and dinaphthenobenzenes, respectively). The AEBP for each data point resembles the mid boiling point of the respective cut. For instance, alkyl benzenes with a weighted average carbon number of 21.3 carbon atoms (including the aromatic ring and alkyl chains) are found in cut #14, which has an average AEBP of 357.5° C. Alkylbenzenes in cut #15 had 21.5 carbon atoms and an average boiling point of 374° C., and so on. As may be seen in FIG. 3 at 305, the average carbon number and boiling temperatures match well with the empirical boiling model for alkylbenzenes.

The other graphs in FIGS. 4-6 show the average data per cut for compounds with an increasing number of aromatic rings, with a good fitness apparent for compounds with up to four aromatic rings. The speciation data for the largest aromatic compound families were of comparably weaker quality (less abundant mass spectrometric signals, some of which may have been lost in the baseline noise), justifying the poorer fit with the model for, for example, AR4 or AR5 depicts. The latter, larger aromatic compounds may be present in significant quantity only in the higher boiling cuts. A similar match between modelled boiling curves and measured data may be obtained for sulfur and disulfur data as shown in FIGS. 5 and 6.

Notably, a number of low DBE disulfur compounds are detected in all samples of this example, and the measured carbon numbers also follow the predicted ones.

Boiling Curve Model Generation

Figure 7A:
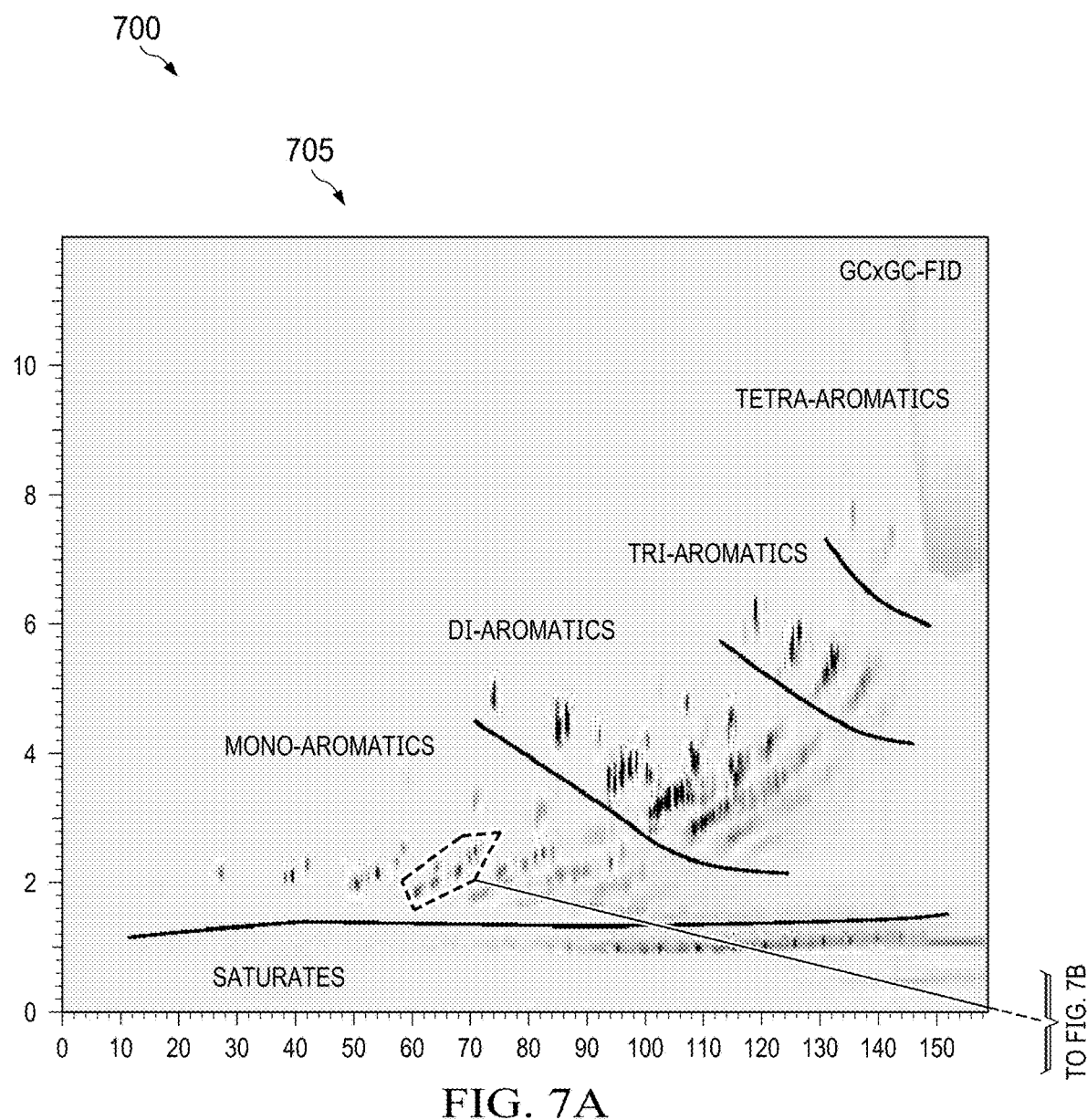
Figure 7C:
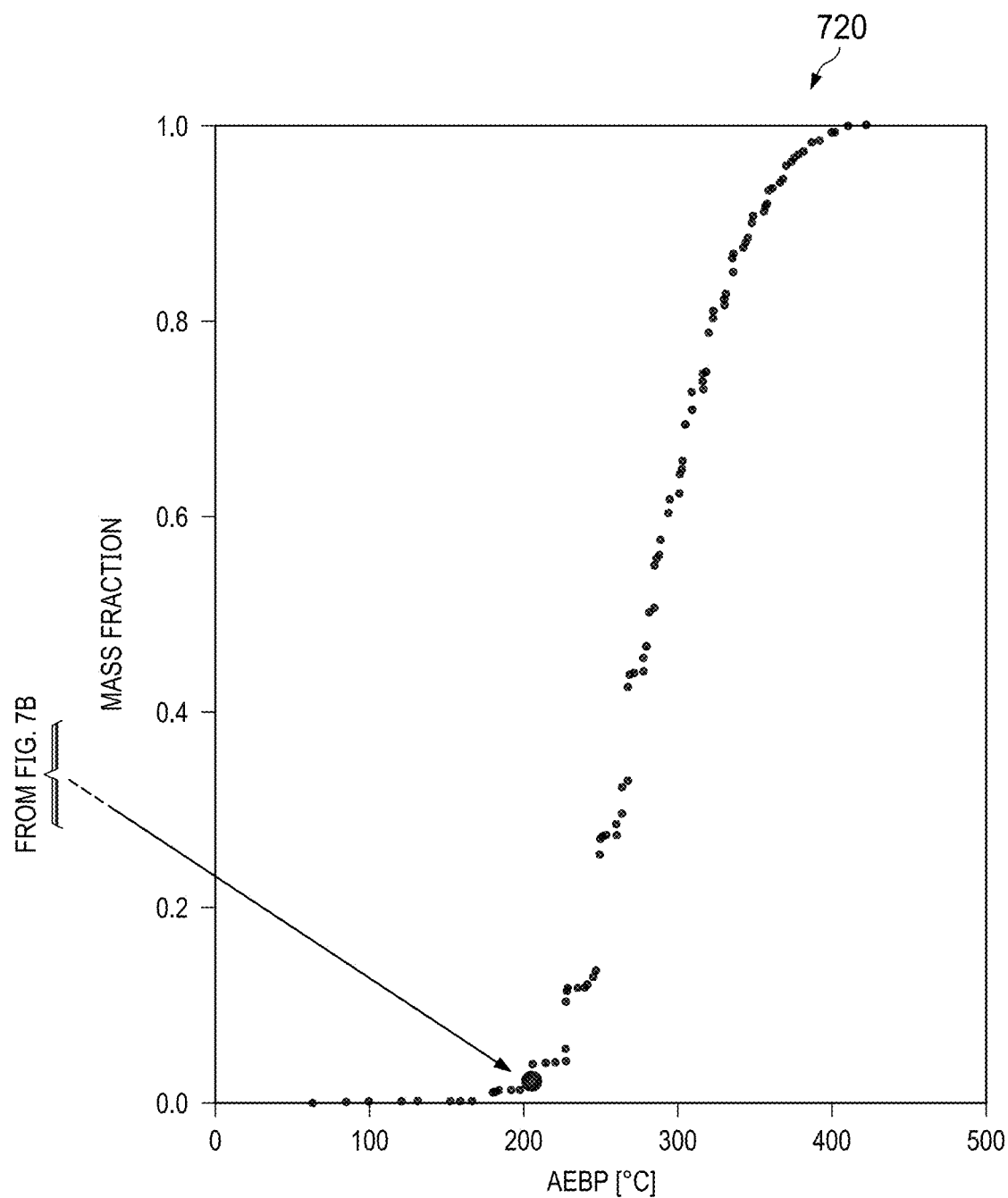

FIGS. 7A, 7B, and 7C collectively depict an example 700 of modeling a boiling curve of a petroleum sample based on the boiling temperatures of the various components of the sample, in accordance with various embodiments.

As discussed above, the example 700 begins with identification of components of the petroleum sample at 705. The X-axis of the graph at 705 represents the first dimension retention time in minutes and the Y-axis of the graph at 705 represents the second dimension retention time in seconds. The 2 dimensional chromatogram depicted at 705 is obtained through GC×GC FID, although in other embodiments the data may be obtained through some other technique such as MS. The components may be identified in accordance with separate AR families, as discussed above.

The data represented in the graph at 705 may then be processed as shown at 710. Specifically, the different components may be generally identified by the number of carbon atoms, the DBE, and the heteroatoms of the components. Specifically, as shown at 710, the components may be separated by carbon number, DBE, and relative FID signal. The number of naphthenic (saturated) and aromatic rings, NR and AR, respectively may be inferred from the DBE and chromatographic retention pattern. Based on this data, the AEBP for each component may be calculated as described above with respect to Equations 1-4a. In this example a low sulfur product stream was speciated by GC×GC FID and sulfur compounds were not considered. Consequently, only pure hydrocarbon molecules were considered (S=0, therefore the A term in equation 3 was set to 0).

The data representing the composition model discussed above with respect to element 115, and AEBP generated at 710 may then be processed as shown at 715. Specifically, the various components may be sorted by their AEBP and the individual mass fractions are then summed to obtain the cumulative boiling curve as shown at 720.

Further Examples

Figure 8A:
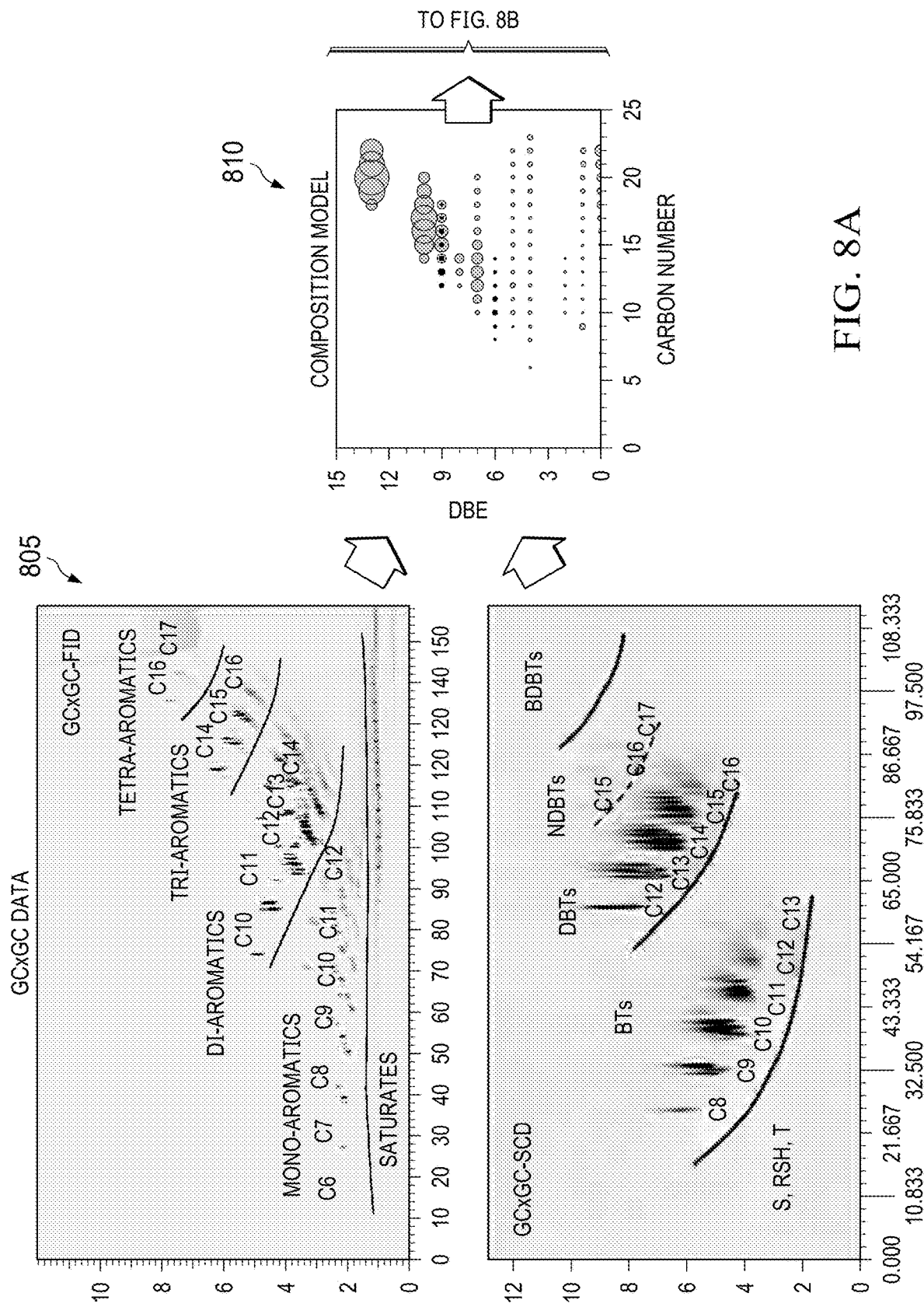
FIGS. 8A and 8B collectively depict an example of modeling a boiling curve and comparing the boiling curve to SIMDIS data, in accordance with various embodiments.
Figure 8B:
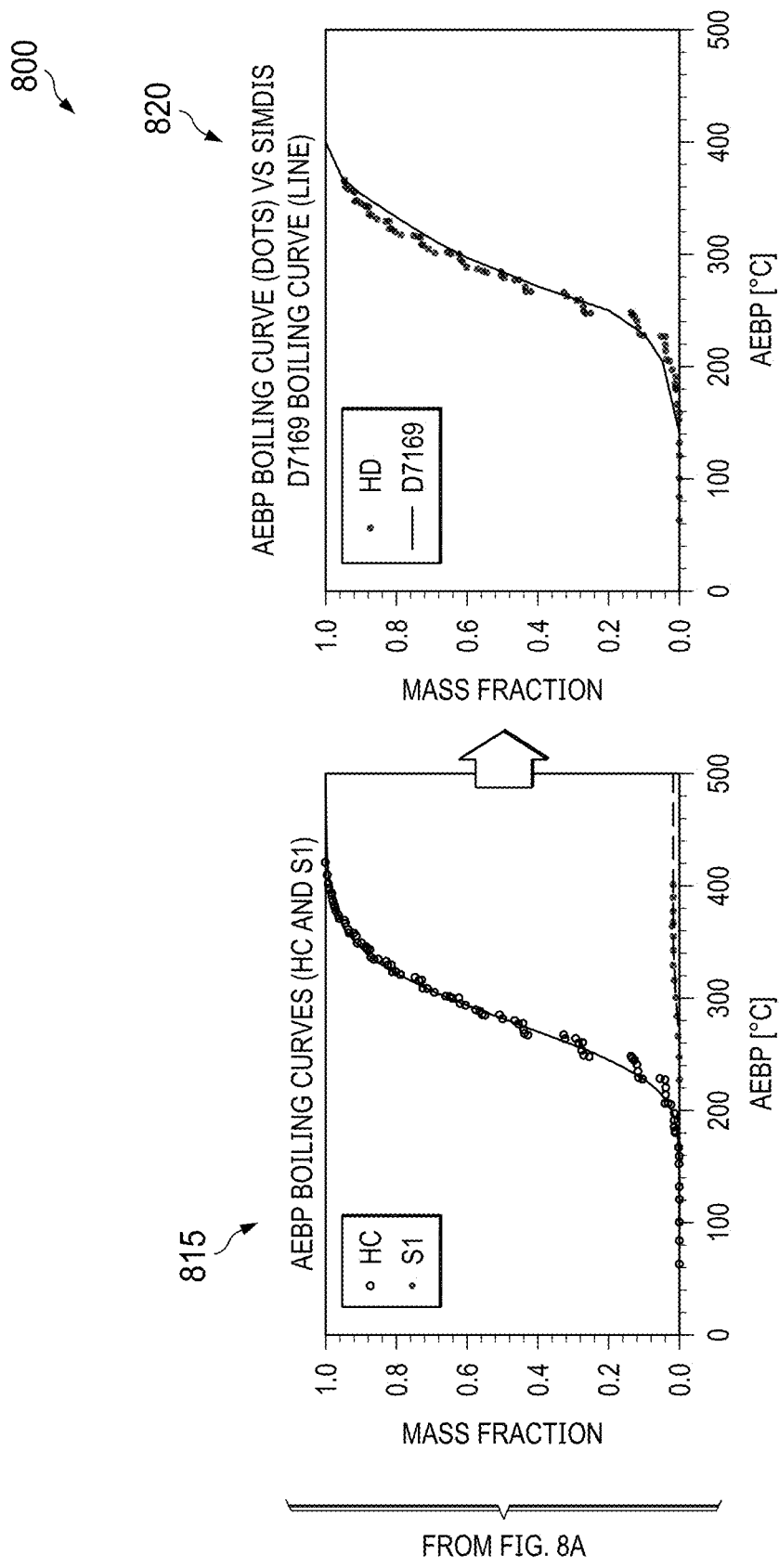

FIGS. 8A and 8B collectively depict an example 800 of modeling a boiling curve and comparing the boiling curve to SIMDIS data, in accordance with various embodiments.

Specifically, as shown at 805, GC×GC data may be generated. The data may be, in this example of a sulfur containing petroleum sample, generated through FID for the identification of the predominant hydrocarbon compounds and include different ARs. The sulfur containing compounds are determined through SCD and include data with different sulfur containing AR families, such as sulfides (S), mercaptans (RSH), thiophenes (T), benzothiophenes (BTs), dibenzothiophenes (DBTs), naphtobenzothiophenes (NDBTs), and Benzonaphthothiophenes (BDBTs). The data from 805 may be used to generate a composition model 810, which may be similar to the composition model discussed above with respect to element 115. The AEBP for respective components may be calculated for both and used to generate an overall boiling curve for selected sub sets of the composition model, for instance HC and S1 class compounds, as depicted at 815 and as discussed above with respect to FIGS. 7A, 7B, and 7C. A combined boiling curve representing the entire composition from 810 may then be compared against a SIMDIS boiling curve as depicted at 820 for verification as previously described. As may be seen in FIGS. 8A and 8B, good agreement between the boiling curve and the SIMDIS data may be obtained, which indicates that the GC×GC data accurately covers the composition of the petroleum sample.

Figure 9A:
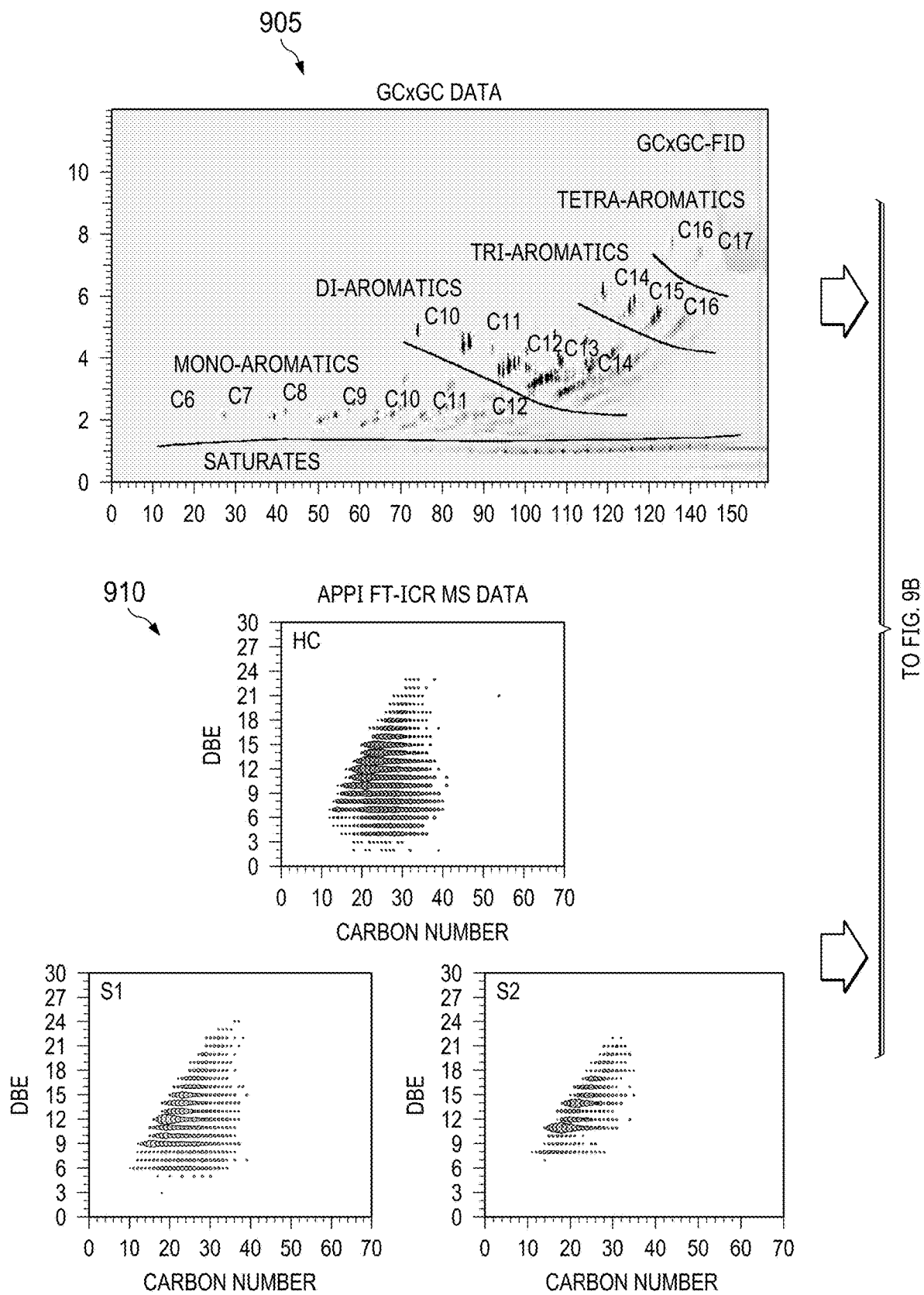
FIGS. 9A and 9B collectively depict alternative examples of modeling a boiling curve and comparing the boiling curve to SIMDIS data, in accordance with various embodiments.
Figure 9B:
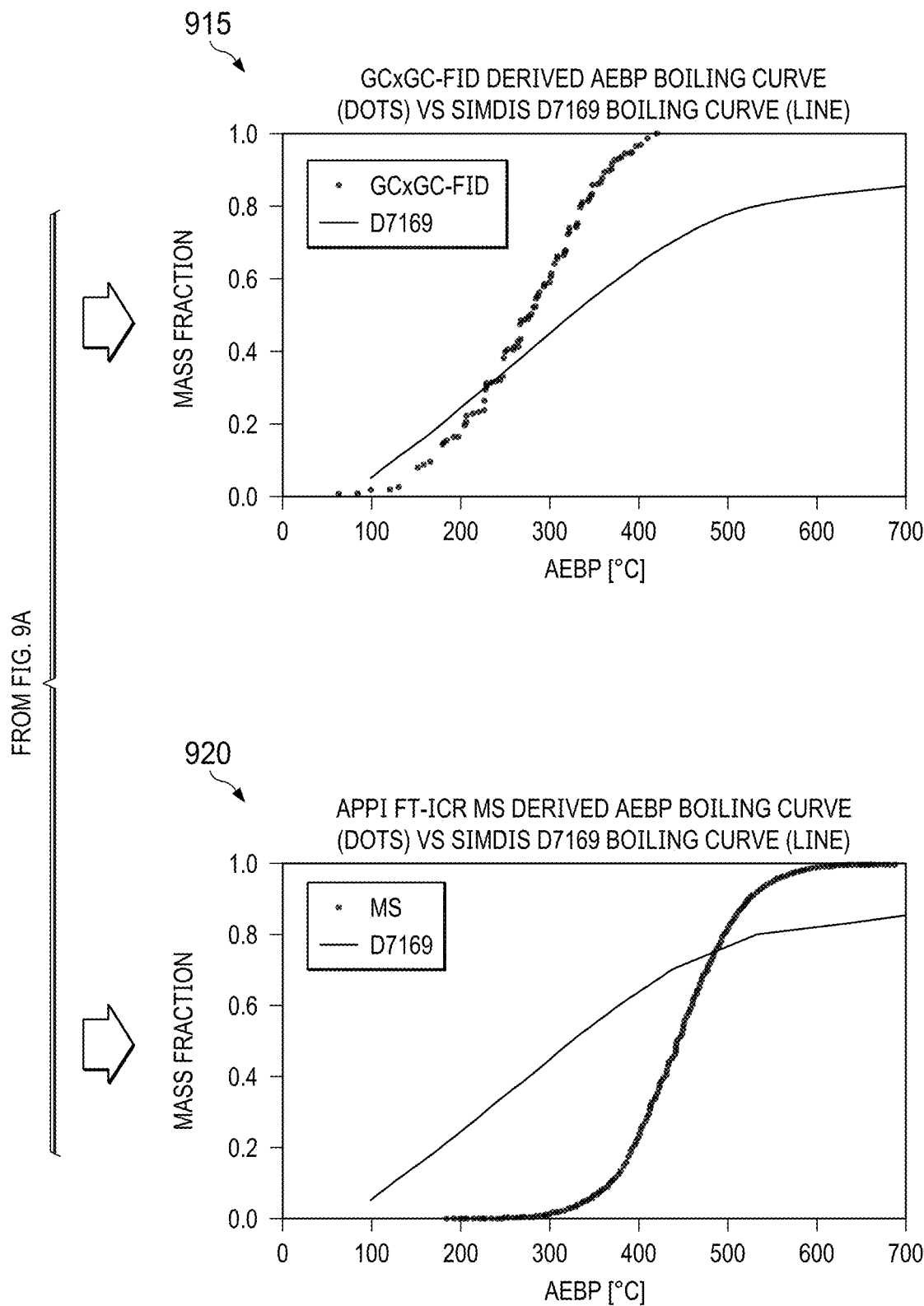

FIGS. 9A and 9B collectively depict alternative examples of modeling a boiling curve and comparing the boiling curve to SIMDIS data, in accordance with various embodiments. Specifically, FIGS. 9A and 9B depict GC×GC composition data 905 (which may be similar to that depicted at 105 or 805) and a resultant AEBP boiling curve of the petroleum sample compared to a SIMDIS boiling curve of the sample at 915 (which may be similar to the comparison at 125 or 820). FIGS. 9A and 9B depict an additional example of MS-based composition data (which may be similar to that depicted at 110). Specifically, the composition data at 910 may be APPI FT-ICR MS data. FIGS. 9A and 9B further depict a resultant AEBP boiling curve of the petroleum sample compared to a SIMDIS boiling curve of the sample at 920 (which may also be similar to the comparison at 125 or 820).

As may be seen in FIGS. 9A and 9B, the AEBP curves based on the compositional data may not have strong correspondence to the SIMDIS curves. This lack of correspondence may indicate, for example, that the GC×GC-based data set 905 does not adequately describe the high-boiling portion of the petroleum sample, leading to the mismatch at 915. Similarly, the APPI FT-ICR MS data set depicted at 910 may not adequately describe the low-boiling components of the petroleum sample, leading to the mismatch at 920. Consequently, it may be identified that neither of the speciation data sets depicted at 905 or 910 adequately describe the composition of the petroleum sample, and hence may not be used as a quantitative description of the petroleum sample.

Technique Overview

Figure 10:
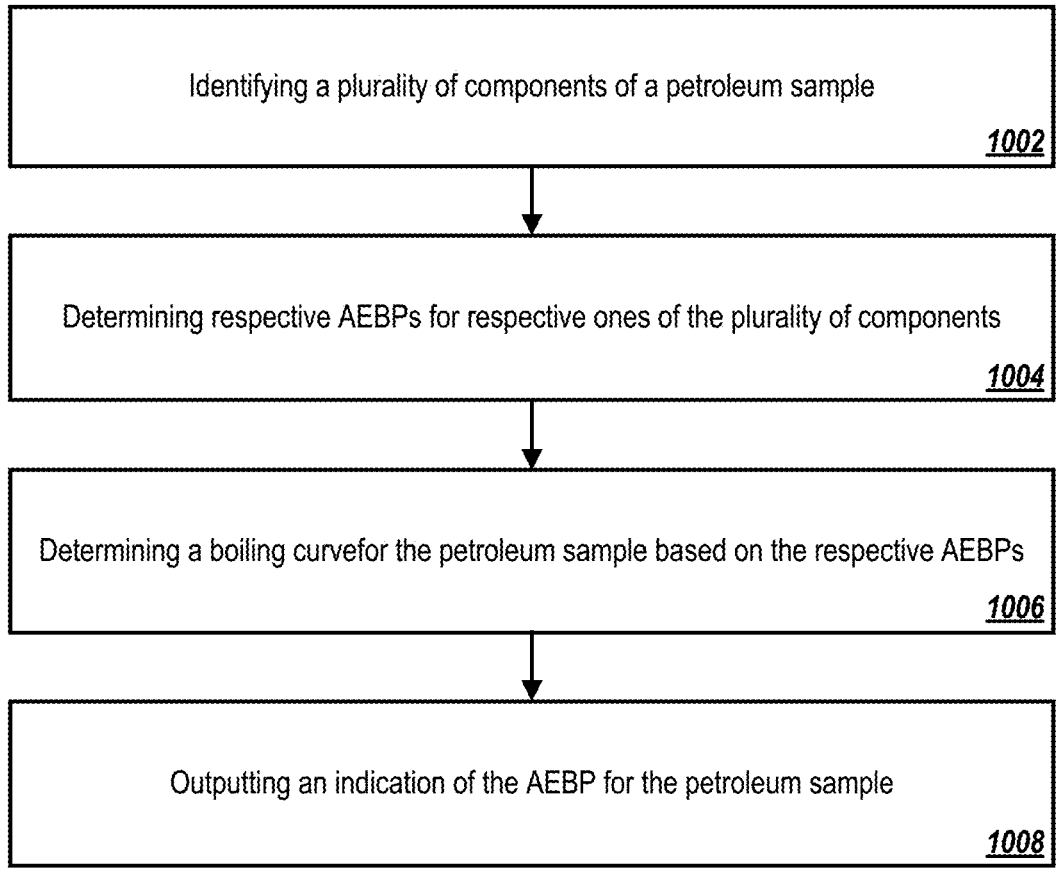
FIG. 10 depicts an example technique for modeling a boiling curve, in accordance with various embodiments.

FIG. 10 depicts an example technique for modeling a boiling curve, in accordance with various embodiments. For clarity of presentation, the description that follows generally describes technique 1000 in the context of the other figures in this description. However, it will be understood that technique 1000 may be performed, for example, by any suitable system, environment, software, and hardware, or a combination of systems, environments, software, and hardware, as appropriate. In some implementations, various elements of technique 1000 may be run in parallel, in combination, in loops, or in any order.

The technique 1000 may include identifying, at 1002, a plurality of components of a petroleum sample. The plurality of components may be identified through, for example, GC×GC, MS, or some other technique as described above or as discussed with respect to, for example, elements 105/110/115/705/805/810/905/910, or elsewhere.

The technique 1000 may further include determining, at 1004, respective AEBPs for respective ones of the plurality of components. The respective AEBPs may be identified as described above with respect to FIGS. 2-6, element 710, or elsewhere. In some embodiments, the AEBPs of the components may be based on one or more of equations 1-4a, as described above. For example, the AEBP of a component of the petroleum sample may be based on a number of carbon atoms in the component, a number of sulfur atoms in the component, and a number of DBEs in the component. The DBEs in the component may be based on the number of carbon atoms in the component, a number of nitrogen atoms in the component, and a number of hydrogen atoms in the component.

The technique 1000 may further include determining, at 1006, a boiling curve for the petroleum sample based on the respective AEBPs. Such a determination may be based on a summation of the respective AEBPs of the respective ones of the plurality of components as described with respect to FIGS. 7A, 7B, and 7C. In some embodiments, the technique may further include comparing the determined boiling curve to a qualitative or semi-quantitative boiling curve that is based on, for example, SIMDIS or an experimentally determined boiling curve of the sample.

The technique 1000 may further include outputting, at 1008, an indication of the boiling curve for the petroleum sample. The outputting may be, for example, displaying the boiling curve on graphical user interface (GUI) of a user display, presenting the boiling curve in a data sheet or spreadsheet, or some other type of output. In some embodiments, the indication of the boiling curve of the petroleum sample may be output to an electronic device for further processing of the petroleum sample based on the boiling curve of the petroleum sample. Such processing may take the form of refinement of the petroleum sample, separation of different parts of the sample, or some other form of processing. In some embodiments, the boiling curve for the petroleum sample may be used to avail a comparison between obtaining a true boiling curve or SIMDIS data and a more advanced technique such as GC, GC×GC, MS, etc. to judge the portion of the sample with the more advanced technique. For example, through such a comparison the suitability of the more advanced technique to identify the components of the petroleum sample may be identified.

Figure 11:
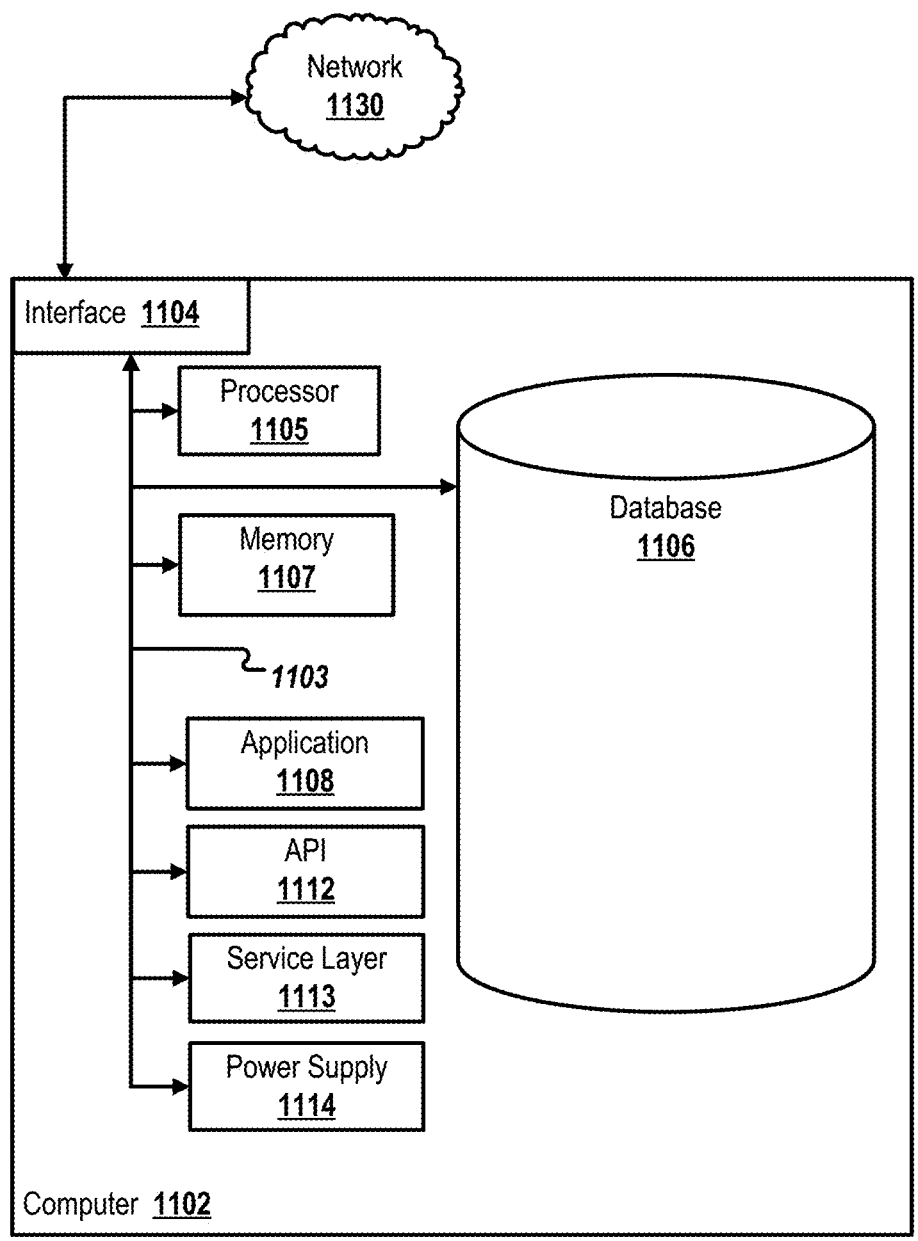
FIG. 11 illustrates an example computer system used to provide computational functionalities associated with described algorithms, methods, functions, processes, flows, and procedures as described in the present disclosure, according to some implementations of the present disclosure.

FIG. 11 is a block diagram of an example computer system 1100 used to provide computational functionalities associated with described algorithms, methods, functions, processes, flows, and procedures described in the present disclosure, according to some implementations of the present disclosure. The illustrated computer 1102 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 1102 can include input devices such as keypads, keyboards, and touch screens that can accept user information. Also, the computer 1102 can include output devices that can convey information associated with the operation of the computer 1102. The information can include digital data, visual data, audio information, or a combination of information. The information can be presented in a graphical user interface (UI) (or GUI).

The computer 1102 can serve in a role as a client, a network component, a server, a database, a persistency, or components of a computer system for performing the subject matter described in the present disclosure. The illustrated computer 1102 is communicably coupled with a network 1130. In some implementations, one or more components of the computer 1102 can be configured to operate within different environments, including cloud-computing-based environments, local environments, global environments, and combinations of environments.

At a top level, the computer 1102 is an electronic computing device operable to receive, transmit, process, store, and manage data and information associated with the described subject matter. According to some implementations, the computer 1102 can also include, or be communicably coupled with, an application server, an email server, a web server, a caching server, a streaming data server, or a combination of servers.

The computer 1102 can receive requests over network 1130 from a client application (for example, executing on another computer 1102). The computer 1102 can respond to the received requests by processing the received requests using software applications. Requests can also be sent to the computer 1102 from internal users (for example, from a command console), external (or third) parties, automated applications, entities, individuals, systems, and computers.

Each of the components of the computer 1102 can communicate using a system bus 1103. In some implementations, any or all of the components of the computer 1102, including hardware or software components, can interface with each other or the interface 1104 (or a combination of both) over the system bus 1103. Interfaces can use an application programming interface (API) 1112, a service layer 1113, or a combination of the API 1112 and service layer 1113. The API 1112 can include specifications for routines, data structures, and object classes. The API 1112 can be either computer-language independent or dependent. The API 1112 can refer to a complete interface, a single function, or a set of APIs.

The service layer 1113 can provide software services to the computer 1102 and other components (whether illustrated or not) that are communicably coupled to the computer 1102. The functionality of the computer 1102 can be accessible for all service consumers using this service layer. Software services, such as those provided by the service layer 1113, can provide reusable, defined functionalities through a defined interface. For example, the interface can be software written in JAVA, C++, or a language providing data in extensible markup language (XML) format. While illustrated as an integrated component of the computer 1102, in alternative implementations, the API 1112 or the service layer 1113 can be stand-alone components in relation to other components of the computer 1102 and other components communicably coupled to the computer 1102. Moreover, any or all parts of the API 1112 or the service layer 1113 can be implemented as child or sub-modules of another software module, enterprise application, or hardware module without departing from the scope of the present disclosure.

The computer 1102 includes an interface 1104. Although illustrated as a single interface 1104 in FIG. 11, two or more interfaces 1104 can be used according to particular needs, desires, or particular implementations of the computer 1102 and the described functionality. The interface 1104 can be used by the computer 1102 for communicating with other systems that are connected to the network 1130 (whether illustrated or not) in a distributed environment. Generally, the interface 1104 can include, or be implemented using, logic encoded in software or hardware (or a combination of software and hardware) operable to communicate with the network 1130. More specifically, the interface 1104 can include software supporting one or more communication protocols associated with communications. As such, the network 1130 or the interface's hardware can be operable to communicate physical signals within and outside of the illustrated computer 1102.

The computer 1102 includes a processor 1105. Although illustrated as a single processor 1105 in FIG. 11, two or more processors 1105 can be used according to particular needs, desires, or particular implementations of the computer 1102 and the described functionality. Generally, the processor 1105 can execute instructions and can manipulate data to perform the operations of the computer 1102, including operations using algorithms, methods, functions, processes, flows, and procedures as described in the present disclosure.

The computer 1102 also includes a database 1106 that can hold data for the computer 1102 and other components connected to the network 1130 (whether illustrated or not). For example, database 1106 can be an in-memory, conventional, or a database storing data consistent with the present disclosure. In some implementations, database 1106 can be a combination of two or more different database types (for example, hybrid in-memory and conventional databases) according to particular needs, desires, or particular implementations of the computer 1102 and the described functionality. Although illustrated as a single database 1106 in FIG. 11, two or more databases (of the same, different, or combination of types) can be used according to particular needs, desires, or particular implementations of the computer 1102 and the described functionality. While database 1106 is illustrated as an internal component of the computer 1102, in alternative implementations, database 1106 can be external to the computer 1102.

The computer 1102 also includes a memory 1107 that can hold data for the computer 1102 or a combination of components connected to the network 1130 (whether illustrated or not). Memory 1107 can store any data consistent with the present disclosure. In some implementations, memory 1107 can be a combination of two or more different types of memory (for example, a combination of semiconductor and magnetic storage) according to particular needs, desires, or particular implementations of the computer 1102 and the described functionality. Although illustrated as a single memory 1107 in FIG. 11, two or more memories 1107 (of the same, different, or combination of types) can be used according to particular needs, desires, or particular implementations of the computer 1102 and the described functionality. While memory 1107 is illustrated as an internal component of the computer 1102, in alternative implementations, memory 1107 can be external to the computer 1102.

The application 1108 can be an algorithmic software engine providing functionality according to particular needs, desires, or particular implementations of the computer 1102 and the described functionality. For example, application 1108 can serve as one or more components, modules, or applications. Further, although illustrated as a single application 1108, the application 1108 can be implemented as multiple applications 1108 on the computer 1102. In addition, although illustrated as internal to the computer 1102, in alternative implementations, the application 1108 can be external to the computer 1102.

The computer 1102 can also include a power supply 1114. The power supply 1114 can include a rechargeable or non-rechargeable battery that can be configured to be either user- or non-user-replaceable. In some implementations, the power supply 1114 can include power-conversion and management circuits, including recharging, standby, and power management functionalities. In some implementations, the power supply 1114 can include a power plug to allow the computer 1102 to be plugged into a wall socket or a power source to, for example, power the computer 1102 or recharge a rechargeable battery.

There can be any number of computers 1102 associated with, or external to, a computer system containing computer 1102, with each computer 1102 communicating over network 1130. Further, the terms "client," "user," and other appropriate terminology can be used interchangeably, as appropriate, without departing from the scope of the present disclosure. Moreover, the present disclosure contemplates that many users can use one computer 1102 and one user can use multiple computers 1102.

Described implementations of the subject matter can include one or more features, alone or in combination.

For example, in a first implementation, a computer-implemented method includes obtaining the boiling point of individual components in complex petroleum samples based on state-of-the-art analytical speciation methods.

The foregoing and other described implementations can each, optionally, include one or more of the following features:

A first feature, combinable with any of the following features, where the composition information is obtained using an ultrahigh resolution mass spectrometer such as a FT-ICR MS with an APPI source, A second feature, combinable with any of the previous or following features, where the composition information is obtained using a high-resolution mass spectrometer such as time of flight MS with a FD/FI source.

A third feature, combinable with any of the previous or following features, where the composition information is obtained using a GC×GC with a FID.

A fourth feature, combinable with any of the previous or following features, where the composition information is obtained using a GC×GC with FID and element selective detection, for instance using a SCD or NCD.

A fifth feature, combinable with any of the previous or following features, where the composition information is obtained using a GC×GC with high-resolution MS detection and data processing algorithms.

A sixth feature, combinable with any of the previous or following features, wherein the techniques of any of the previous or following features are used to judge the fitness of the speciation method for quantitative description of the sample.

A seventh feature, combinable with any of the previous or following features, wherein the techniques of any of the previous or following features are used to quantify the portion of the sample that is characterized by the analytical speciation method.

An eighth feature, combinable with any of the previous or following features, wherein the techniques of any of the previous or following features are used to select the appropriate analytical speciation method based on the boiling curve of the sample established through TBP or simulated distillation.

In a second implementation, a method includes identifying, by an electronic device, a plurality of components of a petroleum sample; determining, by the electronic device, respective atmospheric equivalent boiling points (AEBPs) for respective ones of the plurality of components; determining, by the electronic device, a boiling curve for the petroleum sample based on the respective AEBPs; and outputting, by the electronic device, an indication of the boiling curve for the petroleum sample.

The foregoing and other described implementations can each, optionally, include one or more of the following features:

A first feature, combinable with any of the following features, wherein the boiling curve of the petroleum sample is based on a summation of the respective AEBPs of the respective ones of the plurality of components.

A second feature, combinable with any of the previous or following features, further including comparing, by the electronic device, the determined boiling curve to a boiling curve related to the petroleum sample.

A third feature, combinable with any of the previous or following features, wherein the boiling curve related to the petroleum sample is based on simulated distillation of the petroleum sample.

A fourth feature, combinable with any of the previous or following features, wherein the boiling curve related to the petroleum sample is based on an experimental boiling point curve of the petroleum sample.

A fifth feature, combinable with any of the previous or following features, further including identifying, by the electronic device, the plurality of components of the petroleum sample based on comprehensive two-dimensional gas chromatography of the petroleum sample.

A sixth feature, combinable with any of the previous or following features, further including identifying, by the electronic device, the plurality of components of the petroleum sample based on high-resolution mass spectrometry.

A seventh feature, combinable with any of the previous or following features, wherein an AEBP of a component of the petroleum sample is based on a number of carbon atoms in the component, a number of sulfur atoms in the component, and a number of double bond equivalents (DBEs) in the component.

An eighth feature, combinable with any of the previous or following features, wherein the DBEs in the component are based on the number of carbon atoms in the component, a number of nitrogen atoms in the component, and a number of hydrogen atoms in the component.

A ninth feature, combinable with any of the previous or following features, further including identifying, by the electronic device, a suitability of a technique used to identify the plurality of components of the petroleum sample.

A tenth feature, combinable with any of the previous or following features, wherein the technique to identify the plurality of components of the petroleum sample is gas chromatography, two-dimensional gas chromatography, or mass spectrometry.

An eleventh feature, combinable with any of the previous or following features, further including estimating, by the electronic device based on the respective AEBPs or the boiling curve, at least one boiling data that is outside of a range of the AEBPs or the boiling curve.

A twelfth feature, combinable with any of the previous features, further including processing, by the electronic device, the petroleum sample based on the boiling curve of the petroleum sample.

In a third implementation, at least one non-transitory computer-readable media includes instructions that, upon execution of the instructions by at least one processor of an electronic device, are to cause the electronic device to: identify a plurality of components of a petroleum sample; determine respective atmospheric equivalent boiling points (AEBPs) for respective ones of the plurality of components; determine a boiling curve for the petroleum sample based on the respective AEBPs; and output an indication of the boiling curve for the petroleum sample.

The foregoing and other described implementations can each, optionally, include one or more of the following features:

A first feature, combinable with any of the following features, wherein the boiling curve of the petroleum sample is based on a summation of the respective AEBPs of the respective ones of the plurality of components.

A second feature, combinable with any of the previous or following features, wherein the instructions are further to compare the determined boiling curve to a boiling curve related to the petroleum sample.

A third feature, combinable with any of the previous or following features, wherein the boiling curve related to the petroleum sample is based on simulated distillation of the petroleum sample.

A fourth feature, combinable with any of the previous or following features, wherein the boiling curve related to the petroleum sample is based on an experimental boiling point curve of the petroleum sample.

A fifth feature, combinable with any of the previous or following features, wherein the instructions are further to identify the plurality of components of the petroleum sample based on comprehensive two-dimensional gas chromatography of the petroleum sample.

A sixth feature, combinable with any of the previous or following features, wherein the instructions are further to identify the plurality of components of the petroleum sample based on high-resolution mass spectrometry.

A seventh feature, combinable with any of the previous or following features, wherein an AEBP of a component of the petroleum sample is based on a number of carbon atoms in the component, a number of sulfur atoms in the component, and a number of double bond equivalents (DBEs) in the component.

An eighth feature, combinable with any of the previous or following features, wherein the DBEs in the component are based on the number of carbon atoms in the component, a number of nitrogen atoms in the component, and a number of hydrogen atoms in the component.

A ninth feature, combinable with any of the previous or following features, wherein the instructions are further to identify a suitability of a technique used to identify the plurality of components of the petroleum sample.

A tenth feature, combinable with any of the previous or following features, wherein the technique to identify the plurality of components of the petroleum sample is gas chromatography, two-dimensional gas chromatography, or mass spectrometry.

An eleventh feature, combinable with any of the previous or following features, wherein the instructions are further to estimate, based on the respective AEBPs or the boiling curve, at least one boiling data that is outside of a range of the AEBPs or the boiling curve.

A twelfth feature, combinable with any of the previous features, wherein the instructions are further to process the petroleum sample based on the boiling curve of the petroleum sample.

In another implementation, an electronic device includes at least one processor; and at least one non-transitory computer-readable media including instructions that, upon execution of the instructions by the at least one processors of an electronic device, are to cause the electronic device to: identify a plurality of components of a petroleum sample; determine respective atmospheric equivalent boiling points (AEBPs) for respective ones of the plurality of components; determine a boiling curve for the petroleum sample based on the respective AEBPs; and output an indication of the boiling curve for the petroleum sample.

The foregoing and other described implementations can each, optionally, include one or more of the following features:

A first feature, combinable with any of the following features, wherein the boiling curve of the petroleum sample is based on a summation of the respective AEBPs of the respective ones of the plurality of components.

A second feature, combinable with any of the previous or following features, wherein the instructions are further to compare the determined boiling curve to a boiling curve related to the petroleum sample.

A third feature, combinable with any of the previous or following features, wherein the boiling curve related to the petroleum sample is based on simulated distillation of the petroleum sample.

A fourth feature, combinable with any of the previous or following features, wherein the boiling curve related to the petroleum sample is based on an experimental boiling point curve of the petroleum sample.

A fifth feature, combinable with any of the previous or following features, wherein the instructions are further to identify the plurality of components of the petroleum sample based on comprehensive two-dimensional gas chromatography of the petroleum sample.

A sixth feature, combinable with any of the previous or following features, wherein the instructions are further to identify the plurality of components of the petroleum sample based on high-resolution mass spectrometry.

A seventh feature, combinable with any of the previous or following features, wherein an AEBP of a component of the petroleum sample is based on a number of carbon atoms in the component, a number of sulfur atoms in the component, and a number of double bond equivalents (DBEs) in the component.

An eighth feature, combinable with any of the previous or following features, wherein the DBEs in the component are based on the number of carbon atoms in the component, a number of nitrogen atoms in the component, and a number of hydrogen atoms in the component.

A ninth feature, combinable with any of the previous or following features, wherein the instructions are further to identify a suitability of a technique used to identify the plurality of components of the petroleum sample.

A tenth feature, combinable with any of the previous or following features, wherein the technique to identify the plurality of components of the petroleum sample is gas chromatography, two-dimensional gas chromatography, or mass spectrometry.

An eleventh feature, combinable with any of the previous or following features, wherein the instructions are further to estimate, based on the respective AEBPs or the boiling curve, at least one boiling data that is outside of a range of the AEBPs or the boiling curve.

A twelfth feature, combinable with any of the previous features, wherein the instructions are further to process the petroleum sample based on the boiling curve of the petroleum sample.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/-R, DVD-RAM, DVD-ROM, HD-DVD, and BLU-RAY.

The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A method comprising:
   identifying a plurality of components of a petroleum sample according to at least one speciation technique;
   determining respective atmospheric equivalent boiling points (AEBPs) for respective ones of the plurality of components;
   determining a boiling curve for the petroleum sample based on the respective AEBPs;
   outputting an indication of the boiling curve for the petroleum sample; and
   determining that the at least one speciation technique identifies an entirety of the plurality of components of the petroleum sample or a portion of the plurality of components of the petroleum sample by comparing the determined boiling curve for the petroleum sample with a true boiling curve obtained by actual distillation.

2. The method of claim 1, wherein the boiling curve of the petroleum sample is based on a summation of the respective AEBPs of the respective ones of the plurality of components.

3. The method of claim 1, further comprising comparing, by the electronic device, the determined boiling curve to a boiling curve related to the petroleum sample.

4. The method of claim 1, further comprising identifying, by the electronic device, the plurality of components of the petroleum sample based on comprehensive two-dimensional gas chromatography of the petroleum sample.

5. The method of claim 1, further comprising identifying, by the electronic device, the plurality of components of the petroleum sample based on high-resolution mass spectrometry.

6. The method of claim 1, wherein an AEBP of a component of the petroleum sample is based on a number of carbon atoms in the component, a number of sulfur atoms in the component, and a number of double bond equivalents (DBEs) in the component.

7. The method of claim 1, further comprising identifying, by the electronic device, a suitability of a technique used to identify the plurality of components of the petroleum sample.

8. The method of claim 1, further comprising estimating, by the electronic device based on the respective AEBPs or the boiling curve, at least one boiling data that is outside of a range of the AEBPs or the boiling curve.

9. The method of claim 1, further comprising processing, by the electronic device, the petroleum sample based on the boiling curve of the petroleum sample.

10. D) At least one non-transitory computer-readable media comprising instructions that, upon execution of the instructions by at least one processor of an electronic device, are to cause the electronic device to:
   identify a plurality of components of a petroleum sample according to at least one speciation technique;

determine respective atmospheric equivalent boiling points (AEBPs) for respective ones of the plurality of components;

determine a boiling curve for the petroleum sample based on the respective AEBPs;

output an indication of the boiling curve for the petroleum sample; and determine that the at least one speciation technique identifies an entirety of the plurality of components of the petroleum sample or a portion of the plurality of components of the petroleum sample by comparing the determined boiling curve for the petroleum sample with a true boiling curve obtained by actual distillation.

11. The at least one non-transitory computer-readable media of claim 10, wherein the boiling curve of the petroleum sample is based on a summation of the respective AEBPs of the respective ones of the plurality of components.

12. The at least one non-transitory computer-readable media of claim 10, wherein the instructions are further to compare the determined boiling curve to a boiling curve related to the petroleum sample.

13. The at least one non-transitory computer-readable media of claim 12, wherein the boiling curve related to the petroleum sample is based on simulated distillation of the petroleum sample.

14. The at least one non-transitory computer-readable media of claim 12, wherein the boiling curve related to the petroleum sample is based on an experimental boiling point curve of the petroleum sample.

15. An electronic device comprising:
at least one processor; and
at least one non-transitory computer-readable media comprising instructions that, upon execution of the instructions by the at least one processors of an electronic device, are to cause the electronic device to:
identify a plurality of components of a petroleum sample according to at least one speciation technique;
determine respective atmospheric equivalent boiling points (AEBPs) for respective ones of the plurality of components;
determine a boiling curve for the petroleum sample based on the respective AEBPs;
output an indication of the boiling curve for the petroleum sample; and
determine that the at least one speciation technique identifies an entirety of the plurality of components of the petroleum sample or a portion of the plurality of components of the petroleum sample by comparing the determined boiling curve for the petroleum sample with a true boiling curve obtained by actual distillation.

16. The electronic device of claim 15, wherein an AEBP of a component of the petroleum sample is based on a number of carbon atoms in the component, a number of sulfur atoms in the component, and a number of double bond equivalents (DBEs) in the component.

17. The electronic device of claim 16, wherein the DBEs in the component are based on the number of carbon atoms in the component, a number of nitrogen atoms in the component, and a number of hydrogen atoms in the component.

18. The electronic device of claim 15, wherein the speciation technique to identify the plurality of components of the petroleum sample is gas chromatography, two-dimensional gas chromatography, or mass spectrometry.

19. The electronic device of claim 15, wherein the instructions are further to estimate, based on the respective AEBPs or the boiling curve, at least one boiling data that is outside of a range of the AEBPs or the boiling curve.

20. The electronic device of claim 15, wherein the instructions cause the electronic device to sum the respective AEBPs for respective ones of the plurality of components to determine the boiling curve.

* * * * *